United States Patent [19]

Cornelissen et al.

[11] Patent Number: 5,670,706
[45] Date of Patent: Sep. 23, 1997

[54] FUNGAL RESISTANT PLANTS, PROCESS FOR OBTAINING FUNGAL RESISTANT PLANTS AND RECOMBINANT POLYNUCLEOTIDES FOR USE THEREIN

[75] Inventors: Bernardus J. C. Cornelissen, Warmond; Leo Sjoerd Melchers, Leiden; Elisabeth J. S. Meulenhoff; Jeroen S. C. van Roekel, both of Amsterdam; Marianne Beatrix Sela-Buurlage, Amersfoort; Alexandra Aleida Vloemans, Leiden, all of Netherlands; Charles Peter Woloshuk, Lafayette, Ind.; John Ferdinand Bol, Oegstgeest; Hubertus J. M. Linthorst, Leiden, both of Netherlands

[73] Assignees: MOGEN International, n.v.; Rijksuniversiteit te Leiden, both of Leiden, Netherlands

[21] Appl. No.: 47,413

[22] Filed: Apr. 19, 1993

Related U.S. Application Data

[62] Division of Ser. No. 647,831, Jan. 29, 1991, abandoned.

[51] Int. Cl.⁶ .................. A01H 4/00; C12N 15/82
[52] U.S. Cl. .......... 800/205; 435/320.1; 435/252.3; 435/172.3; 800/DIG. 44
[58] Field of Search .................. 536/23.2, 23.6; 435/320.1, 172.3, 250.3; 800/205, DIG. 43, DIG. 44

[56] References Cited

U.S. PATENT DOCUMENTS

| | | | |
|---|---|---|---|
| 4,801,540 | 1/1989 | Hiatt et al. | 435/172.3 |
| 4,940,840 | 7/1990 | Suslow et al. | 800/205 |

FOREIGN PATENT DOCUMENTS

| | | |
|---|---|---|
| 0270248 | 6/1988 | European Pat. Off. |
| 0292435 | 11/1988 | European Pat. Off. |
| 0332104 | 9/1989 | European Pat. Off. |
| 9007001 | 6/1990 | WIPO |

OTHER PUBLICATIONS

Young et al., *Physiol. Plant Pathol.* (1982) 21:411–423.
Boller et al., *Planta* (1983) 157:22–31.
Mauch et al., *Plant Physiol.* (1988) 88:936–942.
Schlumbaum et al., *Nature* (1986) 324:365–367.
Christ et al., *Physiol. & Mol. Plant Pathol.* (1989) 35:53–65.
Fischer et al., *Physiol. & Mol. Plant Pathol.* (1989) 35:67–83.
Felix et al., *Planta* (1987) 172:386–392.
Memelink et al., *EMBO J.* (1987) 6(12):3579–3583.
Memelink et al., *Plant Mol. Biol.* (1990) 14:119–126.
Shinshi et al (Jan. 1987) Proc. Natl. Acad. Sci., USA, 84:89–93.
Mauch, et al. (1988) Plant Physiology 88:936–942.
De Loose, et al (1988) Gene 70:13–23.
Ohme-Takagi, et al (1990) Plant Mol. Biology 15:941–946.

*Primary Examiner*—Che S. Chereskin
*Attorney, Agent, or Firm*—Morrison & Foerster LLP

[57] ABSTRACT

Plants are provided with improved resistance against pathogenic fungi. They are genetically transformed with one or more polynucleotides which essentially comprise one or more genes encoding plant chitinases and β-1,3-glucanases. Preferred are the intracellular forms of the said hydrolytic enzymes, especially preferred are those forms which are targeted to the apoplastic space of the plant by virtue of the modification of the genes encoding the said enzymes. Particularly preferred are plants exhibiting a relative overexpression of at least one gene encoding a chitinase and one gene encoding a β-1,3-glucanase.

30 Claims, 12 Drawing Sheets

```
                          M  K  F  W  G  S  V  L  A  L  S  F
         GAATTCCTAATAATCGCGAAAAAAATGAAGTTCTGGGGATCAGTATTGGCATTGTCTTTT
              10                  30       ↓        50

V  V  F  L  F  L  T  G  T  L  A  Q  N  V  G  S  I  V  T  S
         GTTGTGTTCTTGTTCCTAACAGGAACACTGGCACAAAATGTTGGTTCTATTGTGACAAGC
              70                  90                110

D  L  F  D  Q  M  L  K  N  R  N  D  A  R  C  F  A  V  R  F
         GACTTATTTGACCAGATGCTTAAAAATAGGAATGATGCTAGATGTTTTGCCGTACGGTTT
              130                 150                170

Y  T  Y  D  A  F  I  A  A  A  N  S  F  P  G  F  G  T  T  G
         TACACTTACGATGCCTTCATAGCTGCTGCCAATTCGTTCCCAGGTTTTGGAACTACTGGT
              190                 210                230

D  D  T  A  R  K  K  E  I  A  A  F  F  G  Q  T  S  H  E  T
         GATGATACTGCCCGTAAGAAAGAAATTGCTGCCTTTTTCGGTCAAACTTCTCATGAAACT
              250                 270                290

T  G  G  T  L  S  P  D  G  P  Y  A  G  G  Y  C  F  L  R  E
         ACTGGTGGTACCTTAAGTCCAGATGGTCCATATGCAGGAGGATATTGCTTTCTTAGAGAA
              310                 330                350

G  N  Q  M  G  N  G  Y  Y  G  R  G  P  I  Q  L  T  G  Q  S
         GGCAATCAAATGGGAAACGGATACTATGGCAGAGGACCCATCCAATTGACAGGCCAATCT
              370                 390                410

N  Y  D  L  A  G  K  A  I  E  Q  D  L  V  N  N  P  D  L  V
         AACTATGACTTAGCTGGGAAAGCTATTGAACAAGACTTAGTTAACAACCCTGATTTAGTA
              430                 450                470

A  T  D  A  T  V  S  F  K  T  A  I  W  F  W  M  T  P  Q  G
         GCAACAGATGCTACTGTATCATTCAAAACAGCAATATGGTTCTGGATGACACCACAGGGT
              490                 510                530

N  K  P  S  C  H  D  V  I  T  G  R  W  T  P  S  A  A  D  T
         AACAAGCCATCTTGCCACGACGTTATCACCGGCCGATGGACGCCATCAGCCGCCGATACA
              550                 570                590

S  A  N  R  V  P  G  Y  G  V  I  T  N  I  I  N  G  G  I  E
         TCGGCGAATCGTGTACCAGGTTATGGTGTCATTACTAACATAATTAATGGTGGAATTGAA
              610                 630                650

C  G  K  G  Q  N  A  R  V  E  D  R  I  G  Y  Y  R  R  N  V
         TGTGGCAAAGGTCAGAATGCACGAGTGGAAGATCGAATTGGATATTACAGGAGGAATGTA
              670                 690                710

S  I  M  N  V  A  P  G  D  N  L  D  C  Y  N  Q  R  N  F  A
         AGTATAATGAACGTGGCCCCTGGAGACAATTTGGATTGTTACAACCAAAGGAACTTTGCC
              730                 750                770
          E  V  *
         GAAGTCTAGGCTGGTCACATTATGAGTGCAAATGTTATGTAGTCATGGAGATGACAGTAT
              790                 810                830
         ACAACTTATATTTGAATGTAATAAATAAGGGATTCTCTATGCCCATTTATGATAGAGTGA
              850                 870                890
         AATATATTATTGTTTGTCTTCTTGGAAAGAAGTAGAACCAACAGTTCCTTTAAAAAAAAGGAATTC
              910                 950
```

FIG. I

```
                  M  R  L  C  K  F  T  A  L  S  S  L  L  F  S  L  L
GGATCCAACATGAGGCTGTGCAAATTCACAGCTCTTTCTTCTCTACTCTTTTCTCTCCTA
         10                30                50

L  L  S  A  S  A  E  Q  C  G  S  Q  A  G  G  A  R  C  A  S
CTCCTCTCTGCCTCGGCAGAACAATGTGGTTCGCAGGCGGGAGGTGCGCGTTGTGCCTCG
         70                90               110

G  L  C  C  S  K  F  G  W  C  G  N  T  N  D  Y  C  G  P  G
GGTCTCTGCTGCAGCAAATTTGGTTGGTGTGGTAACACCAATGACTATTGTGGCCCTGGC
         130               150               170

N  C  Q  S  Q  C  P  G  G  P  T  P  P  G  G  G  D  L  G  S
AATTGCCAGAGCCAGTGCCCTGGTGGTCCCACACCACCCGGTGGTGGGGATCTCGGCAGT
         190               210               230

I  I  S  S  S  M  F  D  Q  M  L  K  H  R  N  D  N  A  C  Q
ATCATCTCAAGTTCCATGTTTGATCAGATGCTTAAGCATCGCAACGATAATGCATGCCAA
         250               270               290

G  K  G  F  Y  S  Y  N  A  F  I  N  A  A  R  S  F  P  G  F
GGAAAGGGATTCTACAGTTACAATGCCTTTATCAATGCTGCTAGGTCTTTTCCTGGCTTT
         310               330               350

G  T  S  G  D  T  T  A  R  K  R  E  I  A  A  F  F  A  Q  T
GGTACTAGTGGTGATACCACTGCCCGTAAAAGAGAAATCGCGGCTTTCTTCGCCCAAACC
         370               390               410

S  H  E  T  T  G  G  W  A  T  A  P  D  G  P  Y  A  W  G  Y
TCCCATGAAACTACAGGAGGATGGGCAACAGCACCAGATGGTCCATACGCGTGGGGTTAC
         430               450               470

C  W  L  R  E  Q  C  S  P  G  D  Y  C  T  P  S  G  Q  W  P
TGCTGGCTTAGAGAACAATGTAGCCCCGGCGACTACTGTACACCAAGTGGTCAGTGGCCT
         490               510               530

C  A  P  G  R  K  Y  F  G  R  G  P  I  Q  I  S  H  N  Y  N
TGTGCTCCTGGTCGGAAATATTTCGGACGAGGCCCCATCCAAATTTCACACAACTACAAC
         550               570               590

Y  G  P  C  G  R  A  I  G  V  D  L  L  N  N  P  D  L  V  A
TACGGACCTTGTGGAAGAGCCATAGGAGTGGACCTCCTAAACAATCCTGATTTAGTGGCC
         610               630               650

T  D  P  V  I  S  F  K  S  A  L  W  F  W  M  T  P  Q  S  P
ACAGATCCAGTAATCTCATTCAAGTCAGCTCTCTGGTTTTGGATGACTCCTCAATCACCA
         670               690               710

K  P  S  C  H  D  V  I  I  G  R  W  Q  P  S  S  A  D  R  A
AAACCTTCTTGCCACGATGTCATCATTGGAAGATGGCAACCATCGTCTGCTGACCGCGCA
         730               750               770

A  N  R  L  P  G  F  G  V  I  T  N  I  I  N  G  G  L  E  C
GCCAATCGTCTCCCTGGATTTGGTGTCATCACGAACATCATCAATGGTGGCTTGGAATGT
         790               810               830
```

FIG. 2A

```
G   R   G   T   D   S   R   V   Q   D   R   I   G   F   Y   R   R   Y   C   S
GGTCGTGGCACTGACTCAAGGGTCCAGGATCGCATTGGGTTTTACAGGAGGTATTGCAGT
      850                 870                 890

I   L   G   V   S   P   G   D   N   L   D   C   G   N   Q   R   S   F   G   N
ATTCTTGGTGTTAGTCCTGGTGACAATCTTGATTGCGGAAACCAGAGGTCTTTTGGAAAC
      910                 930                 950

G   L   L   V   D   T   M   *
GGACTTTTAGTCGATACTATGTAATTTTATGGTCTGTTTTGTTGAATCCCTTTGCGACGC
      970                 990                1010

AGGGACCAGGGGCTATGAATAAAGTTAATGTGTGAATTGTGTGATTGTCATCTATGGGAT
     1030                1050                1070

CGCGACTATAATCGTTTATAATAAACAAAGACTTGTCCACAAAAAAAAAAAGGAATTAAT
     1090                1110                1130

TCCCGGGGATCC
     1150
```

FIG. 2B

```
CTTCTGCTTGTCTATATAAGAAGCAGCCTAATGGTTCCTTAAACACACAATTTCAGCTCA
         10             30             50      M  T  L  C  I  K  N  G  F
AGTGTTTCTTACTCTCTCATTTCCATTTTAGCTATGACTTTATGCATTAAAAATGGCTTT
         70             90             110
  L  A  A  A  L  V  L  V  G  L  L  I  C  S  I  Q  M  I  G___
CTTGCAGCTGCCCTTGTACTTGTTGGGCTGTTAATTTGCAGTATCCAAATGATAGGTCTC
        130            150            170
___ intron
TCTCTCTCACACACACACACTTTCTCTCATGATACATGTACATGCACCTTGTATGATGCG
        190            210            230
GATCAACTTATGTACACTAATAGCGTAAATAATTTTTACAATATATATTAGGATTAATAT
        250            270            290
ATTTTAACATGTTGTGTCAGGTAATCTACCTTATTTATTAAGTCACTTATTATGAATAGT
        310            330            350
TACTTATAGTTACTTCTGGGTGACCCGACACTATAATGTTGGCTAGAGAAGAACTTAAAT
        370            390            410
AGAGAATCATGGTTAGTGAGAATATTCATTTATTCGACACCAACTTATTTGGGGACTGAA
        430            450       ↓    470
                intron            A    Q  S  I  G  V  C  Y
ACTTCTTTGTAATATACTCTTTTTCTTACAATCCAGGGGCACAATCTATTGGAGTATGCT
        490            510            530
   G  K  H  A  N  N  L  P  S  D  Q  D  V  I  N  L  Y  N  A  N
ATGGAAAACATGCAAACAATTTACCATCAGACCAAGATGTTATAAACCTATACAATGCTA
        550            570            590
   G  I  R  K  M  R  I  Y  N  P  D  T  N  V  F  N  A  L  R  G
ATGGCATCAGAAAGATGAGAATCTACAATCCAGATACAAATGTCTTCAACGCTCTCAGAG
        610            630            650
   S  N  I  E  I  I  L  D  V  P  L  Q  D  L  Q  S  L  T  D  P
GAAGTAACATTGAGATCATTCTCGACGTCCCACTTCAAGATCTTCAATCCCTAACTGATC
        670            690            710
   S  R  A  N  G  W  V  Q  D  N  I  I  N  H  F  P  D  V  K  F
CTTCAAGAGCCAATGGATGGGTCCAAGATAACATAATAAATCATTTCCCAGATGTTAAAT
        730            750            770
   K  Y  I  A  V  G  N  E  V  S  P  G  N  N  G  Q  Y  A  P  F
TTAAATATATAGCTGTTGGAAATGAAGTCTCTCCCGGAAATAATGGTCAATATGCACCAT
        790            810            830
   V  A  P  A  M  Q  N  V  Y  N  A  L  A  A  A  G  L  Q  D  Q
TTGTTGCTCCTGCCATGCAAAATGTATATAATGCATTAGCAGCAGCAGGGTTGCAAGATC
        850            870            890
   I  K  V  S  T  A  T  Y  S  G  I  L  A  N  T  Y  P  P  K  D
AAATCAAGGTCTCAACTGCAACATATTCAGGGATCTTAGCGAATACCTACCCGCCCAAAG
        910            930            950
   S  I  F  R  G  E  F  N  S  F  I  N  P  I  I  Q  F  L  V  Q
ATAGTATTTTTCGAGGAGAATTCAATAGTTTCATTAATCCCATAATCCAATTTCTAGTAC
        970            990            1010
   H  N  L  P  L  L  A  N  V  Y  P  Y  F  G  H  I  F  N  T  A
AACATAACCTTCCACTCTTAGCCAATGTCTATCCTTATTTTGGTCACATTTTCAACACTG
       1030            1050            1070
   D  V  P  L  S  Y  A  L  F  T  Q  Q  E  A  N  P  A  G  Y  Q
CTGATGTCCCACTTTCTTATGCTTTGTTCACACAACAAGAAGCAAATCCTGCAGGATATC
       1090            1110            1130
   N  L  F  D  A  L  L  D  S  M  Y  F  A  V  E  K  A  G  G  Q
AAAATCTTTTTGATGCCCTTTTGGATTCTATGTATTTTGCTGTAGAGAAAGCTGGAGGAC
       1150            1170            1190
   N  V  E  I  I  V  S  E  S  G  W  P  S  E  G  N  S  A  A  T
```

FIG. 3A

```
AAAATGTGGAGATTATTGTATCTGAAAGTGGCTGGCCTTCTGAAGGAAACTCTGCAGCAA
     1210                1230                1250
      I   E   N   A   Q   T   Y   Y   E   N   L   I   N   H   V   K   S   G   A   G
CTATTGAAAATGCTCAAACTTACTATGAAAATTTGATTAATCATGTGAAAAGCGGGGCAG
     1270                1290                1310
      T   P   K   K   P   G   K   A   I   E   T   Y   L   F   A   M   F   D   E   N
GAACTCCAAAGAAACCTGGAAAGGCTATAGAAACTTATTTATTTGCCATGTTTGATGAAA
     1330                1350                1370
      N   K   E   G   D   I   T   E   K   H   F   G   L   F   S   P   D   Q   R   A
ATAATAAGGAAGGAGATATCACAGAGAAACACTTTGGACTCTTTTCTCCTGATCAGAGGG
     1390                1410                1430
      K   Y   Q   L   N   F   N
CAAAATATCAACTCAATTTCAATTAATTAATGCATGGTAACATTTATTGATATATATAGT
     1450                1470                1490
GATATGAGTAATAAGGAGAAGTAGAACTGCTATGTTTTTCTCTTCAATTGAAAATGTAAC
     1510                1530                1550
TCTGGTTTCACTTTGATATTTATATGACATATTTATTGAGATCTCGTCTTTTGTTTTAAA
     1570                1590                1610
TTCTTGCCTTCTATTGGCAAATATCTGCGTAATTTTCATTTGTTTTAAAAATTACTAAGC
     1630                1650                1670
CTCAAAAGAGTGACTACCAATATATTCTTGATTATTAATATTCCCCGTGCTTGGGGGACC
     1690                1710                1730
GGGTGAGGTGGGGGGTGGGGGGGATGACGAAAAAGTTAATGAAAAACCGGTTTGCATTG
     1750                1770                1790
GATGCTCTTTTTAACCTCCCCAAAATATGATGGTTTTGTTGTCTTGGAGAGTGTTTAAGC
     1810                1830                1850
TACTTCTTCTCAAGAATTTTCTTGGTCAGTTCTTAACGTAATTGCTTTTAATTTCTTAAT
     1870                1890                1910
TATCGGTAACCCTTCGAAACAAAAGGAAAATTAAGCTAGGAGATGACTCGTATTCATAAT
     1930                1950                1970
GTTTTACCTTGGATCAACCCCGCCTTTATATTTCATACGA
     1990                2010
```

FIG. 3B

```
AATATAAATAGCTCGTTGTTCATCTTAATTCTCCCAACAAGTCTTCCCATCATGTCTACC
         10              30              50
                                  M  A  A  I  T  L  L  G  L  L  L  V
TCACATAAACATAATACTCCTCAAATGGCTGCTATCACACTCCTAGGATTACTACTTGTT
         70              90             110

A  S  S  I  D  I  A  G┌──────→intron
GCCAGCAGCATTGACATAGCAGGTTTCTGGTCAAATATTTGAACTTCCCAGCCAAAAATA
        130             150             170
TTGTCTTATAATTTTGTGTGCGCAAAATTTTAATTTAGTTGATAGTTATTTGCTTATTTT
        190             210             230
TCTTTTCAAATTGCTTGTGTTTTTTTCTCAAATTAACTTGCACCGTATTCATTTAGCGAT
        250             270             290
AGTTATTTGCTCTATTTTGTGTAACACTCACTCACAAACTTTTCAATTTGAGGGGAGGAC
        310             330             350
AGTGAATCTAAGATTGAAATTTATGAGTTTAATTAGACTAATTCCCATTTGATTTATTGG
        370             390             410
CTAGAAGTCAATTATTTGCATAGTGAGTCTTTTAACACACAGATTTGAGTTAAAGCTACT
        430             450             470
ACGTTCGTATTAACCCATAACATATACACCTTCTGTTCTAATTTCTTTGACACTTTTTGT
        490             510             530
TAGTTTGTTCCAAAAAGGACGGACATATTTGATATTTGAGAATACTTTACCTTAACCTTA
        550             570             590
ATAGAATTTTTTATGACATCACATATATTATGGAATATATACGACCATAATTTTCAAATA
        610             630             650
TCTTATAGTCGTACAAATATTATAGCATGTTTAATACCACAACTTTCAAATTCTTCTTTT
        670             690             710
CCTTAAAAACAAAATATGTCACATAAATTAAAATAGAGGAAGTATACTACATCAATCAGC
        730             750             770
CCCTAGTGGAGGGGACCTACTGTAAGTTTTTAAGTTTTCAAGAATTCAGTAATTGATTAG
        790             810             830
GAGCCCGTCTGGACATAAAAAAAAATTCCTTTTTTTCCAAAAAATGCCCACTAAATTTCT
        850             870         ↓   890
        intron ←────────┐ A  Q  S  I  G  V  C  Y  G  M
AACACTATTTTGTAATTCTTATTGAGCAGGGGCTCAATCGATAGGTGTTTGCTATGGAAT
        910             930             950
 L  G  N  N  L  P  N  H  W  E  V  I  Q  L  Y  K  S  R  N  I
GCTAGGCAACAACTTGCCAAATCATTGGGAAGTTATACAGCTCTACAAGTCAAGAAACAT
        970             990            1010
 G  R  L  R  L  Y  D  P  N  H  G  A  L  Q  A  L  K  G  S  N
AGGAAGACTGAGGCTTTATGATCCAAATCATGGAGCTTTACAAGCATTAAAAGGCTCAAA
       1030            1050            1070
  I  E  V  M  L  G  L  P  N  S  D  V  K  H  I  A  S  G  M  E
TATTGAAGTTATGTTAGGACTTCCCAATTCAGATGTGAAGCACATTGCTTCCGGAATGGA
       1090            1110            1130
  H  A  R  W  W  V  Q  K  N  V  K  D  F  W  P  D  V  K  I  K
ACATGCAAGATGGTGGGTACAGAAAAATGTTAAAGATTTCTGGCCAGATGTTAAGATTAA
       1150            1170            1190
  Y  I  A  V  G  N  E  I  S  P  V  T  G  T  S  Y  L  T  S  F
GTATATTGCTGTTGGGAATGAAATCAGCCCTGTCACTGGCACATCTTACCTAACCTCATT
       1210            1230            1250
  L  T  P  A  M  V  N  I  Y  K  A  I  G  E  A  G  L  G  N  N
TCTTACTCCTGCTATGGTAAATATTTACAAAGCAATTGGTGAAGCTGGTTTGGGAAACAA
       1270            1290            1310
```

FIG. 4A

```
I   K   V   S   T   S   V   D   M   T   L   I   G   N   S   Y   P   P   S   Q
CATCAAGGTCTCAACTTCTGTAGACATGACCTTGATTGGAAACTCTTATCCACCATCACA
       1330              1350              1370
   G   S   F   R   N   D   A   R   W   F   V   D   A   I   V   G   F   L   R   D
GGGTTCGTTTAGGAACGATGCTAGGTGGTTTGTTGATGCCATTGTTGGCTTCTTAAGGGA
       1390              1410              1430
   T   R   A   P   L   L   V   N   I   Y   P   Y   F   S   Y   S   G   N   P   G
CACACGTGCACCTTTACTCGTTAACATTTACCCCTATTTCAGTTATTCTGGTAATCCAGG
       1450              1470              1490
   Q   I   S   L   P   Y   S   L   F   T   A   P   N   V   V   Q   D   G   S
CCAGATTTCTCTCCCCTATTCTCTTTTTACAGCACCAAATGTGGTGGTACAAGATGGTTC
       1510              1530              1550
   R   Q   Y   R   N   L   F   D   A   M   L   D   S   V   Y   A   A   L   E   R
CCGCCAATATAGGAACTTATTTGATGCAATGCTGGATTCTGTGTATGCTGCCCTCGAGCG
       1570              1590              1610
   S   G   G   A   S   V   G   I   V   V   S   E   S   G   W   P   S   A   G   A
ATCAGGAGGGGCATCTGTAGGGATTGTTGTGTCCGAGAGTGGCTGGCCATCTGCTGGTGC
       1630              1650              1670
   F   G   A   T   Y   D   N   A   A   T   Y   L   R   N   L   I   Q   H   A   K
ATTTGGAGCCACATATGACAATGCAGCAACTTACTTGAGGAACTTAATTCAACACGCTAA
       1690              1710              1730
   E   G   S   P   R   K   P   G   P   I   E   T   Y   I   F   A   M   F   D   E
AGAGGGTAGCCCAAGAAAGCCTGGACCTATTGAGACCTATATATTTGCCATGTTTGATGA
       1750              1770              1790
   N   N   K   N   P   E   L   E   K   H   F   G   L   F   S   P   N   K   Q   P
GAACAACAAGAACCCTGAACTGGAGAAACATTTTGGATTGTTTTCCCCCAACAAGCAGCC
       1810              1830              1850
   K   Y   N   I   N   F   G   V   S   G   G   V   W   D   S   S   V   E   T   N
CAAATATAATATCAACTTTGGGGTCTCTGGTGGAGTTTGGGACAGTTCAGTTGAAACTAA
       1870              1890              1910
   A   T   A   S   L   V   S   E   M   *
TGCTACTGCTTCTCTCGTAAGTGAGATGTGAGCTGATGAGACACTTGAAATCTCTTTACA
       1930              1950              1970
TACGTATTCCTTGGATGGAAAACCTAGTAAAAACAAGAGAAATTTTTTCTTTATGCAAGA
       1990              2010              2030
TACTAAATAACATTGCATGTCTCTGTAAGTCCTCATGGATTGTTATCCAGTGACGATGCA
       2050              2070              2090
ACTCTGAGTGGTTTTAAATTCCTTTTCTTTGTGATATTGGTAATTTGGCAAGAAACTTTC
       2110              2130              2150
TGTAAGTTTGTGAATTTCATGCATCATTAATTATACATCAGTTCCATGTTTGATCAGATT
       2170              2190              2210
GGGATTTGGTAACTTCAATGTTAGTATTATAATTAGTGTCTTTATCATTGACTATCAATT
       2230              2250              2270
AATCTTTATTTGGCAAGGCTTGATATATTTGAGTTACTCTTAGGTATTTGCAAGCAACTG
       2290              2310              2330
ATCTTTCTTTTATCCCGTTTCTGGCTTAAACCTCATTAGAAATATATTATAATGTCACCT
       2350              2370              2390
ACTCTGTGGTTTAAGACATTCCCTTACATTATAAGGTATTTCACGTCGTATCAGGTCGAA
       2410              2430              2450
AAAAATAATGGTACGCTCTTTCTTATCACAAATTTCTCTAACTTCTAGA
       2470              2490
```

FIG. 4B

Polylinker sequence:

```
        EcoRI   KpnI     SmaI    BamHI  XbaI    XhoI    HindIII
5'   GGAATTCTGGTACCTCCCGGGAGGATCCATCTAGAGCTCGAGTAAGCTTC   3'
                                              SacI
```

Polylinker sequence:

```
        EcoRI   KpnI     SmaI    BamHI  XbaI    XhoI    HindIII
5'   GGAATTCTGGTACCTCCCGGGAGGATCCATCTAGAGCTCGAGTAAGCTTC   3'
                                              SacI
```

FUNGAL RESISTANT PLANTS, PROCESS FOR OBTAINING FUNGAL RESISTANT PLANTS AND RECOMBINANT POLYNUCLEOTIDES FOR USE THEREIN

This application is a continuation-in-part of U.S. Ser. No. 07/647,831 filed 29 Jan. 1991, now abandoned.

FIELD OF THE INVENTION

The invention lies in the area of recombinant DNA technology, especially in conjunction with the genetic manipulation of plants and concerns a process for obtaining fungal resistant plants due to genetic manipulation, as well as genetically manipulated plants and plant cells themselves (including subparts of the genetically manipulated plants as well as progeny obtained by asexual or sexual propagation) and recombinant polynucleotides (DNA or RNA) which can be used for the genetic manipulation.

STATE OF THE ART

Most agricultural and horticultural crops are under a constant threat due to fungal attack. To protect the crops from significant losses due to fungal disease, the crops and sometimes the soil in which the crops are grown are periodically treated with large amounts of fungicides. These fungicides form a heavy burden on costs of crop growing, and more importantly on the environment and the growers. Moreover the treatment is very labour intensive. Therefore, there is a need for less costly and safer methods to protect plants from fungal attack which, preferably, are devoid of the need of repeated human involvement.

Induced resistance

In plants generally several types of resistance against pathogens occur; non-host resistance, "horizontal" or partial resistance and "vertical" resistance. None of these forms of resistance is particularly well understood in molecular terms. In addition to these constitutively expressed forms of resistance there is a resistance mechanism that can be induced by certain pathogenic infections as well as by a number of biotic and abiotic factors. This induced resistance is very broad and is directed against various pathogens, including fungi. This is further illustrated below.

Inoculation of the lower leaves of a hypersensitively reacting tobacco cultivar (*Nicotiana tabacum* cv Samsun NN) with tobacco mosaic virus (TMV) results in the formation of local lesions on the inoculated leaves. The non-inoculated leaves appear resistant to a second infection with TMV after 3 days; this resistance lasts at least twenty days, and an optimal resistance is obtained after 7 days. The resistance against the second infection is also directed to other viruses, such as tobacco necrosis virus, tobacco ringspot virus (Ross & Bozarth, 1960; Ross, 1961), and fungi, such as *Thielaviopsis basicola* (Hecht & Bateman, 1964), *Phytophthora nicotianae* and *Peronospora tabacina* (McIntyre & Dodds, 1979; McIntyre et al., 1981).

The phenomenon of induced resistance has been studied in numerous other host plants and in combination with several other pathogens as well (Kuc, 1982; Sequeira, 1983). The general picture emerging from these studies is that a hypersensitive response is accompanied by resistance against a broad range of pathogens, irrespective of the type of pathogen having caused the first infection.

Proteins expressed concomitant with induced resistance

Together with the resistance a great number of proteins is synthesized, which are absent before infection.

Roughly three categories of proteins can be discerned.
1) Key-enzymes in the synthesis of secondary metabolites, such as phytoalexins, which exhibit an antimicrobial effect, and precursors of lignin, which is used in the reinforcement of plant cell walls after pathogen invasion. These enzymes, or their messenger RNAs are mainly found in cells in the immediate vicinity of the site of infection (Elliston et al., 1976; Cramer et al., 1985; Bell et al., 1986).
2) Hydroxyproline rich glycoproteins (HRGPs) or extensins, which can be incorporated into the cell wall and possibly function there as a matrix for the attachment of aromatic compounds like lignin (Fry, 1986). HRGPs are important structural components of plant cell walls, and their accumulation occurs in reaction to fungi, bacteria and viruses (Mazau & Esquerré-Tugayé, 1986). In contrast to the situation with the key-enzymes mentioned above, HRGPs and their mRNAs are found in substantial amounts in non-infected parts of the plant as well as around the site of infection (Showalter et al., 1985).
3) A third group of induced genes encodes proteins which accumulate both inside the cells and in the apoplastic space. Among these proteins are hydrolytic enzymes such as chitinases and glucanases. After a necrotic infection these enzymes can often be found throughout the plant, including the non-infected parts, in higher concentrations than before infection. Increased synthesis of these enzymes appears to be induced also by microbial elicitors, usually fungal cell wall preparations (Darvill & Albersheim, 1984; Toppan & Esquerré-Tugayé, 1984; Mauch et al., 1984; Chappel et al., 1984; Kombrink & Hahlbrock, 1986; Hedrick et al., 1988).

Structure of fungal cell walls

The cell walls of fungi are known to consist of a number of different carbohydrate polymers. Most fungi, with the exception of the Oomycetes, contain considerable amounts of chitin. Chitin is a polymer of N-acetyl glucosamine molecules which are coupled via β-1,4 linkages and, in fungal cell walls, are often associated with β-1,3/β-1,6 glucan, polymers of glucose with β-1,3 and β-1,6 linkages. Fungi from the group of Zygomycetes do not contain glucans with β-1,3 and β-1,6 linkages, while in most of the Oomycetes the glucans are associated with cellulose (for an overview, vide: Wessels and Sietsma, 1981).

In vitro degradation of isolated fungal cell walls

It has been known for a long time that isolated cell walls of fungi can be degraded in vitro by plant extracts (Hilborn & Farr, 1959; Wargo, 1975; Young & Pegg, 1982) and also by chitinase and β-1,3-glucanase preparations from microbial origin (Skujins et al., 1965; Hunsley & Burnett, 1970; Jones et al., 1974).

More recently a purified endo-β-1,3-glucanase from tomato in combination with an exo-β-1,3-glucanase of fungal origin were shown to be capable of hydrolysing isolated cell walls of the fungus *Verticillium albo-atrum*. Each of the preparations separately did not have activity (Young & Pegg, 1982). A purified β-1,3-glucanase from soybean (Keen & Yoshikawa, 1983), as well as a purified chitinase from bean (Boller et al., 1983) have also been shown to be capable of degrading isolated cell walls of fungi in vitro. When pea chitinase and β-1,3-glucanase were tested on isolated cell walls of *Fusarium solani*, both appeared to be active; in combination they appeared to work synergistically (Mauch et al., 1988b).

It is not known whether these hydrolytic enzymes can degrade the polymer compounds in cell walls of living fungi effectively, if at all.

Inhibition of fungal growth on synthetic media by chitinases and glucanases from plant origin Some chitinases and glucanases of plant origin are capable of inhibiting the growth of fungi on synthetic media. Chitinase purified from bean is capable of inhibiting the growth of the fungus *Trichoderma viride* in agar plate assays (Schlumbaum et al., 1986). A combination of chitinase and β-1,3-glucanase, both purified from pea pods, do inhibit the growth of some fungi on agar plates, whereas other fungi are not inhibited. The Ascomycete *Cladosporium cucumerinum* appeared slightly sensitive, while the Oomycetes *Phythophthora cactorum*, *Pythium aphanidermatum* and *Pythium ultimum* are insensitive. Pea chitinase alone has effect on the growth of *T.viride*, while β-1,3-glucanase inhibits the growth of Fusarium f.sp. pisi. It was established that in these assays the inhibition of fungal growth was due to lysis of the hyphal tips (Mauch et al., 1988b). Apparently the hydrolytic enzymes do have access to their substrate in the cell walls of living fungi, when grown on synthetic media, although at least some of the active plant hydrolytic enzymes seem to be specific to certain fungi.

Little is known about the effect of hydrolytic enzymes on fungi in the biotrope, i.e. in the soil or on plant leaves, and although some of these enzymes are putative candidates for a role in fungal resistance, evidently, not all chitinases and glucanases have activity against living fungi.

Possibly, the stage and site of infection at which hydrolytic enzymes come into contact with the invading fungus may be of great importance.

Occurrence of chitinases and glucanases in plants

As far as known, chitinases and β-1,3-glucanases occur in most if not all plant species; both in monocotyledonous and dicotyledonous plants. At least two classes of chitinases and two classes of glucanases can be discriminated: intracellular and extracellular. Both chitinase and glucanase genes of one particular class appears to be encoded by gene families.

Natural expression of chitinases genes and glucanase genes in plants

Chitinase and glucanase genes are known to be expressed in plants both constitutively and in a strictly regulated fashion.

Chitinases and β-1,3-glucanases are constitutively synthesised in roots of tobacco plants (Felix and Meins, 1986, Shinshi et al., 1987,; Memelink et al., 1987, 1989). Nevertheless tobacco plants are not resistant to infection of *Phytophthora parasitica* var. nicotianae (a root pathogen of tobacco). However, resistance against this pathogen can be induced in tobacco plants, following inoculation with TMV (McIntyre & Dodds, 1979). This suggests that a complex of yet unknown factors other than, or in addition to, chitinases and glucanases, may be involved in fungal resistance.

On the other hand, plant species are known which seem to be resistant to fungal infection, although no significant increase in the levels of chitinases or glucanases can be observed. For instance, in tomato a compatible interaction with the fungus *Phytophthora infestans* causes a systemic resistance (Christ & Mösinger, 1989), i.e. a resistance to infection throughout the whole plant, although chitinases or glucanases cannot be detected in such leaves (Fischer et al., 1989). Apparently there is no clear correlation between expression of the genes encoding hydrolytic enzymes and fungal resistance.

In addition to these observations, some chitinases exhibit a regulated expression pattern which does not immediately suggest a correlation with fungal resistance.

For example, genes encoding chitinases are known to be expressed in a developmentally regulated manner in, inter alia, tobacco flowers (Lotan et al., 1989). Glucanases are known to occur in large quantities in seedlings of barley (Swegle et al., 1989; Woodward & Fincher, 1982; Hoj et al., 1988, 1989).

In tobacco cell suspensions the synthesis of intracellular chitinases and glucanases can be inhibited by the addition of cytokinins or auxins (Mohnen et al., 1985; Felix & Meins, 1986; Shinshi et al., 1987; Bauw et al., 1987).

The synthesis of the same hydrolytic enzymes can be induced by cytokinin when this hormone is added to the growth medium in which normal tobacco plants are grown axenically. Under certain circumstances the plant hormone ethylene can also induce the synthesis of chitinase and glucanase (Felix & Meins, 1987).

In the roots and lower leaves of both soil-grown and axenically grown tobacco plants, intracellular chitinases and glucanases can be detected, while in upper leaves they can not be detected at all, or to a much lesser extent (Felix & Meins, 1986; Shinshi et al., 1987; Memelink 1987, 1989). Thus, there is also organ-specific expression of the intracellular chitinases and glucanases.

The regulation of expression of the genes coding for extracellular chitinases and glucanases is hardly, or not at all, influenced by cytokinin (Memelink et al., 1987, 1989). In tobacco flowers the extracellular chitinases are expressed specifically in anthers, sepals and the ovary.

Thus, there is at least an organ-specific expression of the genes coding for the extracellular chitinases as well.

Fungal resistant plants expressing chimeric chitinase genes

Notwithstanding the many still unelucidated features concerning the nature and the role of hydrolytic enzymes in fungal resistance, some initial successes have been reported in providing plants with diminished sensitivity to fungal attack.

In U.S. Pat. No. 4,940,840, tobacco plants expressing a bacterial chitinase gene (i.e. the chiA gene from *Serratia marcescens*) have been shown to be less sensitive to the fungus *Alternaria longipes*.

In the International Patent Application WO 9007001 the plant species tobacco and canola, expressing a bean chitinase under regulation of a strong viral promoter or a plant promoter, appear to be less sensitive to two of the tested fungi, namely *Botrytis cinerea* and *Rhizoctonia solani*. It is not known, however, whether these plants are effectively resistant to other fungi as well.

In European Patent Application EP-A-0 292 435 it was suggested that resistance to certain classes of fungi may be conferred by the introduction of a gene that expresses chitinase in the plant tissues.

Mention was made of a preference in certain cases to target gene products into the mitochondria, the vacuoles, into the endoplasmic vesicles or other cell parts or even into the intercellular (apoplastic) spaces.

There was no teaching of the type of chitinase or of the preferred site of action of the chitinase, in order to obtain the desired effect.

EP-A-0 270 248 proposes a mechanism to target a bacterial gene (the β-glucuronidase gene from *E.coli*) to the plant cell wall by using the leader sequence of the polygalacturonase gene from tomato. It was, inter alia, proposed to target chitinases or glucanases to the plant cell wall to combat fungal attack. Results were not shown, nor was indicated which hydrolytic enzymes should be used, or how intracellular plant proteins must be targeted outside the plant cell.

In the EP-A-0 332 104 genetic constructs are described comprising chemically regulative sequences derived from plant genes, among which the so-called PR-genes, including those coding for chitinase and glucanase. No results of fungal resistant plants were shown.

Summary of the state of the art

Plants contain at least two classes of chitinases and β-1,3-glucanases: extracellular and intracellular. The expression of the genes encoding the said hydrolytic enzymes is not constitutive, at least not in all tissues, but is among other things regulated in a developmental or tissue-specific fashion. However, the expression of the genes can also be induced under certain stress-conditions, such as an infection by a necrotisizing pathogen. In most cases, induction of the synthesis of chitinases and β-1,3-glucanases is accompanied by the induction of resistance against a broad range of pathogens, including phytopathogenic fungi. Whether there is a causal relation between fungal resistance and expression of the genes encoding hydrolytic enzymes is not clear.

Cell walls of phytopathogenic fungi contain glucans and often a certain amount of chitin. These carbohydrate polymers are substrates for glucanases and chitinases, respectively. It is attractive to hypothesize that both hydrolytic enzymes are responsible for the observed resistance. However, this is far from obvious, in view of many observations which are clearly in conflict with this hypothesis.

Hence, it is still far from clear whether hydrolytic enzymes have a significant role in fungal resistance, or, when they appear to have so, how substantial their role in fungal resistance is. It seems at least doubtful that any chitinase can confer broad range protection of plants against phytopathogenic fungi. Generally, it is even questionable if chitinases and glucanases by themselves are capable of providing sufficient protection against a broad range of plant pathogenic fungi.

There is still little basic understanding of the role of hydrolytic enzymes in the complex process of acquiring (induced) fungal resistance. However, there is a need for a method to effectively protect plants against (a broad range) of phytopathogenic fungi, by means of genetic modification.

SUMMARY OF THE INVENTION

The aim of the present invention is to provide plants which have improved resistance to fungal attack. Thereto, plants are genetically transformed by introducing into the genome of the said plants at least one recombinant DNA-construct comprising one or more genes encoding an intracellular chitinase of plant origin, under the control of a promoter which is not naturally associated with that gene.

More in particular the invention provides plants having improved resistance to fungal attack, by virtue of the expression of at least one recombinant DNA-construct that comprises a DNA-sequence, encoding at least one intracellular plant chitinase, which is modified such that the intracellular chitinase becomes secreted into the apoplastic space.

In a preferred embodiment, the invention provides plants exhibiting a more effective protection against fungal attack due to the expression a gene encoding a chitinase, preferably an intracellular chitinase, and a gene encoding a glucanase, under the control of a promoter that allows suitably strong expression, in one or more tissues.

In a still further preferred embodiment, the invention provides plants constitutively expressing a gene encoding an intracellular chitinase of plant origin which is targeted to the apoplastic space and, additionally, one or more genes encoding a hydrolytic enzyme from the group consisting of intracellular chitinases, extracellular chitinases, intracellular glucanases and extracellular glucanases.

One especially preferred embodiment is a plant expressing the genes encoding an intracellular chitinase, an extracellular chitinase, an intracellular β-1,3-glucanase, and an extracellular β-1,3-glucanase. Of these, genes encoding the intracellular forms of the mentioned plant hydrolytic enzymes are particularly preferred. Still more preferred is the use of the genes encoding intracellular hydrolytic enzymes, modified by genetic manipulation as to provide for apoplast targeting. In order to achieve apoplast-targeting of the intracellular hydrolytic enzymes, the 3'-end of the gene encoding the C-terminal end of the intracellular hydrolytic enzymes is modified in order to establish, upon expression of the genes, the absence of the C-terminal amino acids that are involved in intracellular targeting of the respective enzymes. Generally such modification results in the absence of at least 3 amino acids of the C-terminal end, or as many amino acids as desired, as long as the enzymatic function and/or other relevant domains of the protein are not negatively affected. Preferably such modification results in the deletion of between 3 and 25 amino acids in the case of intracellular β-1,3-glucanases, and between 3 and 10 amino acids in the case of intracellular chitinases. More preferred are deletions of 4-8 amino acids.

Further embodiments of the invention are the recombinant DNA molecules, comprising one or more plant expressible DNA sequences encoding at least one intracellular chitinase of plant origin which is modified to achieve targeting of the chitinase to the intercellular space, and, if desired additional DNA sequences encoding one or more hydrolytic enzymes selected from the group consisting of extracellular chitinases, intracellular glucanases and extracellular glucanases.

Certain preferred embodiments are the intracellular chitinase genes located on the EcoRI-SstI fragment of pMOG200; the extracellular chitinase gene from petunia hybrida, located on pMOG200; the intracellular β-1,3-glucanase gene located on the XbaI-SstI fragment of pMOG212; the gene encoding the extracellular β-1,3-glucanase which is located on the SstI-HindIII fragment of pMOG212, or genes which are essentially homologous to the said genes.

Especially preferred are modified versions of the genes encoding intracellular forms of the said hydrolytic enzymes, which provide for apoplast-targeting. This includes the modified intracellular chitinase gene of pMOG189 (or truncated forms thereof which retain antifungal activity), as well as modified forms of intracellular chitinase genes, which are essentially homologous to the intracellular chitinase gene of pMOG189. Also preferred is the modified intracellular glucanase gene of pMOG512, in which a stopcodon is introduced into the coding region to provide for apoplast-targeting of the produced intracellular β-1,3-glucanase.

Also claimed are cloning-, expression-, and transformation vectors containing DNA-sequences comprising the said genes, as well as microorganisms containing said DNA-sequences.

Of these vectors the plasmids pMOG200 and pMOG212, and derivates thereof are preferred.

Further embodiments of the present invention include whole fungal resistant plants obtained by the processes according to the said invention, protoplasts, cells, parts (such as seeds, fruits, leafs, flowers, and the like), and any other part of the plant that can be reproduced either sexually, asexually or both, and progeny of the said plants.

The advantages and the field of application will be readily understood from the following detailed description of the invention.

DESCRIPTION OF THE FIGURES

FIG. 1 (SEQ ID NO:8 and SEQ ID NO:9) shows the nucleotide sequence and the deduced amino acid sequence of a complete cDNA corresponding to an extracellular chitinase from Petunia hybrida. The vertical arrow shows the cleavage site of the signal peptide.

FIG. 2 (SEQ ID NO:10 and SEQ ID NO:11) shows the nucleotide sequence and the deduced amino acid sequence of a BamHI DNA fragment corresponding to an intracellular chitinase from tobacco. The sequence of nucleotide 2 through 22 originates from a synthetic fragment, while the nucleotides 23–27 form the remainder of the EcoRI recognition site. The PstI recognition site (5'-CTGCAG-3') is found at position 129–134. The last 21 nucleotides of the sequence succesively represent a filled in EcoRI recognition site, originating from an EcoRI linker-molecule used for the construction of the cDNA library, a SmaI and a BamHI recognition site, both originating from the polylinker of pIC19H. The arrow shows the cleavage site of the signal peptide.

FIG. 3 (SEQ ID NO:12 and SEQ ID NO:13) shows the nucleotide sequence and the deduced amino acid sequence of a gene coding for an extracellular β-1,3-glucanase from tobacco. The vertical arrow shows the location in the amino acid sequence where the signal peptide is cleaved. The position of the intron is indicated; the sequence of the intron is only given in part.

FIG. 4 (SEQ ID NO:14 and SEQ ID NO:15) shows the nucleotide sequence and the deduced amino acid sequence of a gene coding for an intracellular β-1,3-glucanase from tobacco. The vertical arrow shows the location in the amino acid sequence where the signal peptide is cleaved.

DEFINITIONS

Figure 5:
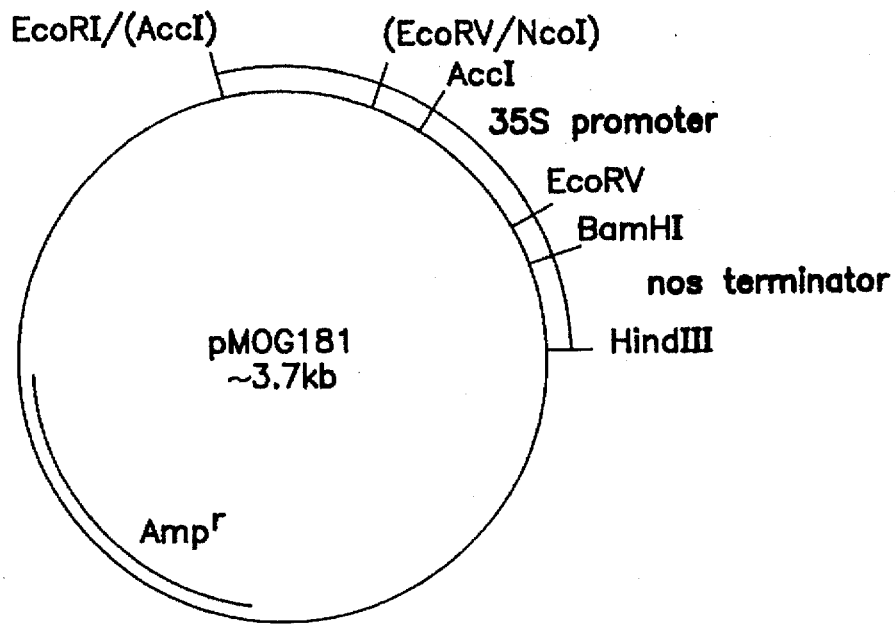
FIG. 5 shows a schematic representation of expression vector pMOG181. Amp$^r$ stands for the ampicilline resistance gene. A restriction enzyme recognition site between brackets shows that the concerned site is no longer present in the plasmid.

For the purpose of the present invention it is understood that an extracellular protein is a protein which after proper expression in the original plant, is localised in the apoplastic space.

Consequently, an intracellular protein is a protein which after proper expression in the plant of origin, is localised intracellularly.

The apoplastic space is defined herein as the extracellular space, including the plant cell wall.

For the purpose of this invention a protein is said to be localised intracellularly if it is localised in any compartment of the cell that does not form part of the apoplastic space; these compartments include nuclei, chloroplasts, mitochondria, vacuoles, endoplasmatic reticulum, other membranous organelles, the cytoplasm, and all membranes, including the plasma membrane.

Genes are said to be essentially homologous if their DNA sequences correspond for more than 60%, unless stated otherwise.

DETAILED DESCRIPTION OF THE INVENTION

In the light of their assumed involvement in fungal resistance, it was surprisingly found that purified extracellular chitinases from tobacco and petunia do not have a significant antifungal effect when compared to intracellular chitinases. In an antifungal assay, equal amounts of chitinolytic activity of purified intracellular and extracellular chitinases, rather than equal amounts of protein, were compared. The antifungal activity of the tested extracellular forms was practically undetectable.

Expression of a chimeric gene encoding an extracellular chitinase in a transformed plant as such, is therefor not sufficient to provide for fungal resistance. Nevertheless, it can not be entirely excluded that extracellular chitinases play a supportive role in fungal resistance, by increasing the antifungal effect of other hydrolytic enzymes present. This observation has important implications for the engineering of fungal resistance in plants, based on expression of chimeric genes encoding plant hydrolytic enzymes.

Comparison of the C-terminal ends of several homologous proteins (particularly of chitinases, and glucanases), which differ essentially in their localisation, revealed that intracellular proteins often have an extension of about 3 to 25 (in the case of intracellular β-1,3-glucanases), or 3 to 10 (in the case of intracellular chitinases) amino acid residues compared to their extracellular analogues. It was surprisingly found, that deletion of about 6 amino acid residues at the C-terminal portion of an intracellular tobacco chitinase results in secretion of the protein to the apoplastic space. Apparently the C-terminal extension functions as a 'vacuole-targeting' signal.

We believe this is the first demonstration of apoplast targeting of chitinases that naturally occur in the vacuole of a plant cell. This finding can be suitably applied for the targeting of vacuolar proteins (e.g. proteins which are localised in the vacuole) to the apoplastic space.

A very effective site of action of hydrolytic enzymes in the protection of transformed plants against a range of plant pathogenic fungi is believed to be the apoplastic space. Hence, to obtain improved fungal resistance it is advantageous if plants are transformed with a recombinant DNA construct comprising a gene encoding a chitinase (or a truncated form thereof, which comprises the antifungal domains or parts) which exerts its action in the apoplastic space of the plant, either naturally or by virtue of genetic modification.

To obtain such plants, it is preferred that plants are transformed with a recombinant DNA construct comprising a gene encoding an intracellular chitinase, which is modified such that the C-terminal amino acids involved in vacuolar targeting are not present (e.g. by introducing a translational stopcodon in the coding region of the gene, or otherwise), resulting in apoplast-targeting of (most of) the intracellular chitinase produced in that plant.

To evaluate the possibility of targeting intracellular hydrolytic enzymes to the apoplastic space, without a significant adverse effect on the antifungal activity, the following experiment was carried out.

Plants were transformed with DNA constructs essentially comprising the following genes:
1) a gene encoding a petunia extracellular chitinase,
2) a gene encoding a tobacco intracellular chitinase,
3) a tobacco gene encoding an intracellular chitinase, modified as to obtain apoplast-targeting of the chitinase (targeting construct), or
4) the petunia extracellular chitinase gene, and the modified tobacco intracellular chitinase gene (targeting-construct).

All genes were placed under the control of the cauliflower mosaic virus 35S promoter. Of each category of the transformed plants good expressors of the chimeric genes were selected and subjected to isolation of extracellular fluids (EF) and total protein extracts (TE) of leaves. The antifungal effect of the different fractions from the plants 1 through 4 were determined on the test fungus *Fusarium solani*. Neither the EF nor the TE of plant 1, expressing the petunia extracellular chitinase had any antifungal activity, as was expected from the experiments using the purified hydrolytic enzymes. The EF of plant 2 had residual antifungal effect (probably due to leakage from the cell of the (relatively over-)expressed intracellular chitinase), whereas the total protein extract showed a strong antifungal effect. Of plant 3, expressing the modified apoplast-targeted intracellular chitinase gene, both the EF and the TE exhibited a strong antifungal effect; this, most importantly, proves that the targeted intracellular chitinase of plant 3 still has antifungal activity. Thus, unexpectedly, the deletion of the C-terminal vacuole targeting signal does not significantly affect the antifungal activity of the chitinase.

Plants may be even more effectively protected against fungal attack if they express both an intracellular chitinase and a modified (apoplast-targeted) intracellular chitinase.

Thus the invention provides plants having improved fungal resistance, as well as methods to obtain such plants.

In a first aspect of the present invention it has been found that the intracellular forms of tobacco and Petunia chitinases are preferred over extracellular chitinases. Therefore, intracellular chitinases are preferred which are essentially homologous to the intracellular chitinases of tobacco. Preferably this homology of intracellular plant chitinases should be larger than 50% on the protein level, more preferably more than 60%, most preferably more than 70%.

A second aspect of the invention is the unexpected finding that the strong antifungal effect of intracellular chitinases is retained after modification of the C-terminal end of the protein. Thus, to improve fungal resistance in transformed plants the most potent hydrolytic enzymes, i.e. the intracellular forms, are selected, and these hydrolytic enzymes, or the truncated forms, which comprise the active antifungal domains/parts, and targeted to the apoplastic space, where their antifungal effect is optimal.

In a following series of experiments the combined effect of chitinases and glucanases in total protein extracts and extracellular fluids of leaves of transgenic plants was investigated.

Tobacco plants were transformed with a recombinant DNA construct essentially comprising:
1) a gene encoding a tobacco intracellular $\beta$-1,3-glucanase, targeted to the apoplast by modification of the C-terminal end;
2) a gene encoding a tobacco intracellular chitinase, and the tobacco intracellular $\beta$-1,3-glucanase, both targeted to the apoplast, by modification of the C-terminal end of the hydrolytic enzymes.

Again, transgenic tobacco plants that were good expressors of the chimeric genes were selected, and subjected to isolation of extracellular fluid (EF) and total protein extract (TE) of leaves. Both the EF and TE of plant 1, expressing the intracellular $\beta$-1,3-glucanase that was targeted to the apoplast, exhibited a weak antifungal effect on the fungus *Fusarium solani*. The EF and TE of plant 2, expressing both the apoplast-targeted intracellular chitinase and the apoplast-targeted intracellular $\beta$-1,2-glucanase, exhibited a surprisingly strong antifungal effect; this effect was slightly higher than that of the EF and TE of plant 3 of the former experiment (expressing only the gene encoding the apoplast-targeted intracellular chitinase).

It can be concluded from these experiments that modification of the C-terminal end of the intracellular $\beta$-1,3-glucanase succesfully leads to apoplast-targeting of (most of) the enzyme, and that the C-terminal modification does not adversely affects the antifungal activity of the intracellular $\beta$-1,3-glucanase. Moreover, it is shown that the antifungal effect of the expression of both an intracellular chimeric chitinase gene and an intracellular chimeric $\beta$-1, 3-glucanase gene is larger than the effect of the expression of each of the genes alone.

Thus, in a third aspect of the invention plants are provided, expressing a chimeric plant chitinase gene and a chimeric plant glucanase gene, both under the regulation of the CaMV 35S promoter.

In a preferred embodiment of the present invention plants are provided which have been transformed with one or more genes encoding intracellular forms of plant hydrolytic enzymes, in a plant expressible form. Especially preferred are plants which express one or more genes encoding intracellular forms of plant hydrolytic enzymes, which by virtue of modification of the C-terminal end are targeted to the apoplast. Still further preferred are plants which are transformed with at least a gene encoding an intracellular chitinase gene and an intracellular $\beta$-1,3-glucanase gene. It will be advantageous if these latter plants express the modified forms of the hydrolytic enzymes, to achieve apoplast-targeting of the said enzymes.

Another preferred embodiment of the invention is a plant constitutively expressing an intracellular chitinase, preferably targeted to the apoplast, an extracellular chitinase, an intracellular glucanase, preferably targeted to the apoplast, and an extracellular glucanase.

In principle any combination of genes encoding plant hydrolytic enzymes can be chosen, modified or unmodified, as long as suitably high expression of these genes does not impair cell function of the transformed plant host. In addition to genes encoding plant hydrolytic enzymes, other plant or non-plant genes (e.g. derived from bacteria, yeast, fungi, or other sources) may be used as well.

The plant genes encoding the hydrolytic enzymes may either be endogenous or exogenous to the plant that is to be transformed.

It will be readily understood, that, in addition to the chitinase and β-1,3-glucanase genes mentioned, genes encoding hydrolytic enzymes can be readily isolated from other plant species as well. Moreover, the genes as meant by the present invention may be entirely synthetic.

Genes or cDNAs coding for the desired hydrolytic enzymes can for instance be isolated from tobacco (e.g. Legrand et al., 1987; Shinshi et al., 1987), tomato (Joosten et al., 1989), a basic intracellular chitinase can be isolated from potato (Gaynor, 1988; Kombrink et al., 1988), an extracellular chitinase can be isolated from cucumber (Métraux & Boller, 1986; Métraux et al., 1986), and both intracellular chitinases and glucanases can be isolated from bean (Broglie et al., 1986; Vögeli et al., 1988; Mauch & Staehelin, 1989).

Furthermore, chitinases and β-1,3-glucanases can be isolated from pea, using chitosan as inducing compound (Mauch et al., 1984). Further analysis revealed the presence of at least five hydrolases, viz. two basic β-1,3-glucanases and three basic chitinases (Mauch et al., 1988a). Intracellular and extracellular chitinases which are serologically related to an intracellular chitinase from bean can be isolated from *Allium porrum* L. (Spanu et al., 1989). Endochitinases and glucanases can also be isolated from maize, following inoculation of leaves with BMV (bromine mosaic virus) (Nasser et al., 1988). Chitinases which are serologically related to an intracellular endochitinase from bean (Swegle et al., 1989) can be isolated from barley (*Hordeum vulgare*). Also β-1,3-glucanases, as well as other classes of glucanases, can be isolated from barley (Balance et al., 1976; Hoj et al., 1988, 1989). At least 4 different chitinases and 5 different β-1,3-glucanases are known to exist in oat (Fink et al., 1988).

It will be understood that sources for obtaining hydrolytic enzymes for protecting plants against fungal attack, are not limited to the list given above, which is only given as illustration.

cDNAs encoding plant chitinases and β-1,3-glucanases are suitably obtained by immunological screening of a cDNA-expression library, made on polyA⁺-RNA, isolated from plants after induction of the synthesis of the hydrolytic enzymes, using an antibody against the desired hydrolytic enzyme. In order to be expressed properly the gene must be operatively linked to a promoter.

The choice of the promoter is dependent on the desired level of expression and the desired way of regulation of the gene under its control. This is all within ordinary skill.

Preferably strong constitutive promoters are used which function throughout the whole plant, with as little as possible restrictions with respect to developmental patterns. One example of a constitutive promoter for high level expression is the CaMV 35S promoter. This promoter may be flanked by so-called enhancer sequences (Mc.Guilley et al., 1987) to further enhance expression levels. Other examples of high-level, light-inducible, promoters are, among others, the ribulose bisphosphate carboxylase small subunit (rbcSSU) promoter, the chlorophyl a/b binding protein (Cab) promoter, and the like. Occasionally, it may be desirable to restrict expression of the introduced chimeric genes to one or a few pre-selected tissues, for instance those that are targets for fungal attack, such as roots and epidermal cells, and the like. A well known example of a tissue-specific promoter is for example the root-specific patatin class-II promoter. Expression of chimeric genes may be dependent on exogenous stimuli as well, like wounding, drought, temperature, and the like.

Generally the gene(s) of choice is/are contained in an expression cassette, which comprises at least a promoter and a transcription terminator, which may be foreign to the gene. It is well known how such elements should be linked in order to function properly and this can be determined without practising inventive skill. Occasionally eukaryotic (genomic) genes contain introns. The presence of the latter, either naturally or introduced by genetic modification, is not particularly relevant to the invention. The techniques for gene manipulation are readily available to a person skilled in the art (vide e.g.: Maniatis et al., 1989).

In addition to genes encoding hydrolytic enzymes also genes encoding other proteins having an extra effect on pathogen resistance may be introduced in the plant of interest, in order to improve the effect or broaden pathogen range. Such proteins are suitably chosen from the group consisting of e.g. lectins, cow pea trypsin inhibitor (CpTI), *Bacillus thuringiensis* toxins, and the like.

To obtain transgenic plants capable of constitutively expressing more than one chimeric gene, a number of alternatives are available, which are encompass by the present invention, including the following:

A. the use of one DNA fragment or plasmid with a number of modified genes physically coupled to one selection marker gene.

B. Cross-pollination of transgenic plants which are already capable of expressing one or more chimeric genes coupled to a gene encoding a selection marker, with pollen from a transgenic plant which contains one or more gene constructions coupled to another selection marker. Afterwards the seed, which is obtained by this crossing, is selected on the basis of the presence of the two markers. The plants obtained from the selected seeds can afterwards be used for further crossing.

C. The use of a number of various DNA fragments of plasmids, each having one or more chimeric genes and one other selection marker. If the frequency of cotransformation is high, then selection on the basis of only one marker is sufficient. In other cases, the selection on the basis of more than one marker is preferred.

D. Consecutive transformations of transgenic plants with new, additional chimeric genes and selection marker genes.

E. Combinations of the above mentioned strategies. The actual strategy is not critical with respect to the described invention and can be easily determined depending on factors such as the desired construct, the materials available and the preference of the skilled workers.

For the transformation of plants several techniques are available. The choice of the technique is generally not critical to the invention, as long as the transforming genetic construct, comprising the genes and regulatory elements according to the invention, can be introduced into a plant and become stably integrated into the genome of that plant. By plant is meant any dicotyledonous or monocotyledonous plant, including progeny, or parts of such plants, cells or protoplasts, and the like, and any other plant material that is amenable to transformation and subsequent regeneration into a whole plant.

Some examples for purposes of illustration are transformation of protoplasts using the calcium/polyethylene glycol method (Krens et al., 1982; Negrutiu et al., 1981), electroporation (ref.) and microinjection (Crossway et al., 1986), (coated) particle bombardment (Klein et al., 1987), infection with viruses and the like. After selection and/or screening for the tranformed plant material, the transformed material is regenerated into whole plants, using methods known in the art.

Subsequently transformed plants are evaluated for the presence of the desired properties and/or the extent to which the desired properties are expressed. A first evaluation may include the level of expression of the newly introduced genes, the level of fungal resistance of the transformed plants, stable heritability of the desired properties, field trials and the like.

Secondly, if desirable, the transformed plants can be cross-bred with other varieties, for instance varieties of higher commercial value or varieties in which other desired characteristics have already been introduced, or used for the creation of hybrid seeds, or be subject to another round of transformation and the like.

Plants, or parts thereof of commercial interest, with improved resistance against phytopathogenic fungi can be grown in the field or in greenhouses, and subsequently be used for animal feed, direct consumption by humans, for prolonged storage, used in food—or other industrial processing, and the like. The advantages of the plants, or parts thereof, according to the invention are the decreased need for fungicide treatment, thus lowering costs of material, labour, and environmental pollution, or prolonged shelf-life of products (e.g. fruit, seed, and the like) of such plants.

Any plant species or variety that is subject to some form of fungal attack may be transformed with one or more genetic constructs according to the invention in order to decrease the rate of infectivity and/or the effects of such attack. As a matter of illustration the species of the following, non-limitative, list are of particular interest: edible flowers, such as cauliflower (*Brassica oleracea*), artichoke (*Cynara scolymus*) (edible flowers); decorative flowers, such as Chrysanthemum, lily, Rosa; edible fruit, such as apple (e.g. *Malus domesticus*), banana, berries (e.g. currant, *Ribes rubrum*), sweet cherry (*Prunus avium*), cucumber (*Cucumis sativus*), grape (*Vitis vinifera*), lemon (*Citrus limon*), melon (*Cucumis sativus*), nuts (e.g. walnut *Juglans regia*), orange, peaches (*Prunus persica*), pear (*Pyra communis*), pepper (*Solanum capsicum*), prunes (*Prunus domestica*), strawberry (Fragaria), tobacco (Nicotiana), tomato (e.g, *Lycopersicon esculentum*); leaf(y) vegetables, such as cabbages (Brassica), endive (*Cichoreum endivia*), lettuce (*Lactuca sativa*), spinach (*Spinacia oleraceae*), leek (*Allium porrum*); edible roots, such as beet (*Beta vulgaris*), carrot (*Daucus carota*), turnip/swede (*Brassica rapa*), radish (*Raphanus sativus*) (edible roots); edible seeds, such as bean (Phaseolus), pea (*Pisum sativum*), soybean (*Glycin max*), wheat (*Triticum aestivum*), barley (*Hordeum vulgare*), corn (*Zea mays*), rice (Oryza); edible tubers, such as kohlrabi, potato (*Solanum tuberosum*), and the like.

The following enabling Examples serve to further illustrate the invention, and are not intended to define limitations or restrict the scope of the subject invention.

EXPERIMENTAL

EXAMPLE 1

Assay for antifungal activity

The effect of various protein solutions on fungal growth was assessed in a microtiter plate assay. In each well of a 24-well microtiter dish 250 μl potato dextrose agar (PDA) was pipetted. Fungal spores were suspended in water and 300–500 spores in 50 μl were added to the wells. Spores were pregerminated overnight. Subsequently 100 μl filter sterilized (0.22 μm filter) protein solutions were added. As controls proteins were boiled for 10 minutes. Microtiter dishes were covered with Parafilm and incubated at room temperature. After 1–2 days the mycelium of the growing fungus in the wells was stained with lactophenol cotton blue and the extent of growth was estimated.

EXAMPLE 2

Assay for chitinase activity

Chitinase activity was assayed radiometrically with tritiated chitin as substrate (Molano et al., 1977) Tritiated chitin was synthesized by acytelation of chitosan with tritiated anhydride (Molano et al., 1977). The specific activity of the final product was approximately $1.2 \times 10^6$ cpm/mg. Before use the tritiated chitin was washed three times. To 100 μl 10 mM potassium phosphate buffer pH 6.4 with 0.02% sodium azide, 50 μl tritiated chitin (approximately 150,000 cpm) and 50 μl protein solution was added. The mixture was incubated shaking for 30 minutes at 37° C. The reaction was stopped by adding 600 μl 10% trichloro acetic acid. After centrifugation to pellet the chitin (10 minutes in a microfuge), 500 μl supernatant was filtered over glasswool and pipetted into a scintillation vial. 5 ml scintillation fluid was added and the radioactivity was counted. The amount of radioactivity released (expressed as counts per minute) was taken as a measure for chitinase activity.

EXAMPLE 3

Antifungal activity of chitinase

Antifungal activity of chitinases was assessed by the microtiter plate assay described above using the fungus *Fusarium solani*. Two purified extracellular tobacco chitinases (also known as pathogenesis-related proteins P and Q), a purified intracellular tobacco chitinase (32 kd protein) and a purified extracellular petunia chitinase were tested. In all cases the added activity was approximately 2000 counts per minute (meaning that this activitiy releases 2000 cpm from tritiated chitin in the chitinase assay). This activity is within in the range in which there is a linearity between protein concentration and activity. As controls bovine serum albumin (BSA), buffer or heat-inactivated chitinase was added. The results are shown in Table 1.

TABLE 1

| Inhibition of the growth of *Fusarium solani* by chitinases. | |
|---|---|
| Protein added | inhibition |
| petunia extracellular chitinase | − |
| petunia extracellular chitinase, boiled | − |
| tobabco extracellular chitinase (PR-P) | − |
| tobacco PR-P, boiled | − |
| tobacco extracellular chitinase (PR-Q) | − |
| tobacco PR-Q, boiled | − |

TABLE 1-continued

Inhibition of the growth of *Fusarium solani* by chitinases.

| Protein added | inhibition |
| --- | --- |
| tobacco intracellular 32 kd chitinase | + |
| tobacco 32 kd intracellular chitinase, boiled | − |
| BSA | − |
| buffer | − |

−: no inhibition; +: inhibition

From the results in Table I it can be concluded that the extracellular chitinases of tobacco and of petunia do not possess antifungal activity.

EXAMPLE 4

4.0 The cloning of cDNAs corresponding with chitinase

Polyadenylated RNA was isolated from TMV-infected Samsun NN tobacco and double stranded cDNA was made using oligo (dT) as a primer (Hooft van Huijsduijnen et al., 1986) using standard techniques known to researchers in this area. The double stranded DNA was provided with "C-tails" which were hybridized with "G-tails" which were brought into the plasmid pUC9 after this plasmid was spliced open with PstI (Maniatis et al., 1982). The constructs obtained were used for the transformation of *Escherichia coli* MH-1. The transformants were brought in duplo on nitrocellulose filters. The first filter was hybridized in vitro with transcribed cDNA of poly(A)-RNA from TMV-infected tobacco, the other filter was hybridized with cDNA against poly(A)-RNA from healthy tobacco (Maniatis et al., 1982). Transformants which showed better hybridization with the first probe than with the second contained cDNA corresponding with mRNAs whose synthesis was induced via the TMV infection. The cDNA clones obtained could be subdivided into six clusters on the basis of cross-hybridizations of the insertions: within a cluster, the insertions of all clones hybridize with each other, between clusters no cross-hybridizations took place (Hooft van Huijsduijnen et al., 1986) under the hybridization and wash conditions used (0.1 SSC, 1% SDS, 65° C.; Maniatis et al., 1982). The TMV-inducibility of the synthesis of mRNAs corresponding with the insertions of the clones of the six clusters, were confirmed via Northern blot analyses, well known to researchers in this area (Hooft van Huijsduijnen et al., 1986).

Via immunoprecipitations of in vitro translation-products of mRNAs by means of selective hybridization with (the insertions of) cDNA clones from the six clusters, it was established that the clones of two clusters, namely clusters D and F, correspond with mRNAs for proteins serologically related to the so-called PR-proteins P and Q (Hooft van Huisduijnen et al., 1987). The experiments were conducted according to standard techniques known to researchers in this area. The PR-proteins P and Q were already earlier identified as extracellular acidic chitinases, and antibodies against both proteins cross-react with two basic chitinases also present in tobacco (Legrand et al., 1987). Inserts of clones from clusters D and F were subcloned in M13-vectors and the sequence of the insertions was determined by the method of Sanger et al. (1977). One clone from cluster F, namely PROB3, appeared to contain an insertion of 412 base-pairs, wherein an open reading frame occurs, coding for 109 amino acids wherefrom the sequence appears to be identical to the C-terminal sequence of a basic chitinase of tobacco (Hooft van Huijsduijnen et al., 1987). The amino acid sequence of this chitinase was determined from the nucleotide-sequence of a cDNA clone, namely pCHN50 (Shinshi et al., 1987). Cluster F, including clone PROB3, consequently corresponds with one or more intracellular basic chitinases of tobacco.

Cluster D contains one clone, namely PROB30, with an insertion of 404 base-pairs, wherein an open reading frame occurs, coding for 67 amino acids (Hooft van Huijsduijnen et al., 1987). The homology between the amino acid sequences deduced from the nucleotide-sequences of the insertions of PROB3 and PROB30 appears to be 65%, while the nucleotide-sequences themselves showed a homology of only 56%. From this it was concluded that PROB30 corresponds with a chitinase that is related to, but is not identical to the intracellular chitinase. After partial amino acid sequences for PR-proteins P and Q were established, it was concluded that PROB30 corresponds with PR-protein P, an extracellular acidic chitinase of tobacco.

4.1 Construction of cDNA clones coding for an entire extracellular chitinase

To obtain cDNA clones containing the entire coding sequence for the chitinases, clone PROB30 was used as a probe for the selection of clones from a *Petunia hybrida* cDNA library. Double stranded cDNA was synthesized as described above, treated with EcoRI-methylase, provided with EcoRI-linkers, ligated to lambda gt11 vector-arms and transfected to *E. coli* Y1090 entirely according to the method described in the instruction manual belonging to "cDNA cloning system-lambda gt11" (Amersham International plc, 1986). Afterwards, the newly constructed library was searched with the plaque hybridization-technique of Benton and Davis (1977) whereby the previously described acidic chitinase-cDNA clone served as a probe. In this manner, five recombinant phages were obtained with sequences homologous to PROB30. Recombinant phage DNA was isolated and afterwards the insertions were spliced out with EcoRI and subcloned in a pUC plasmid, resulting in the clones, D1, D2, D5, D6 and D8. After being subcloned in sections into M13-phages, the nucleotide sequences of the original insertions were entirely or partially determined. In FIG. 1, the sequence of clone D1 and a deduced amino acid sequence are provided. The first and the last 7 nucleotides originate from the EcoRI-linkers which were used for the construction of the library. The sequence of eight A-residues at the end of the insertion, just before the EcoRI recognition site represent the remainder of the poly(A)-tail of the original mRNA and consequently confirms the orientation of the insertion previously assigned through the large open reading frame and the homology to the deduced amino acid sequence of other chitinases (see above). The insertion of clone D5 appears to be 10 nucleotides longer on its 5' extremity than that of D1; the remainder of the poly(A)-tail was however, as with the insertion of D6,found 25 nucleotides earlier in the sequence. For as far as could be traced, the sequences of the insertions of D8, D2 and D6 appeared to be identical to those of D1 and D5.

The homology between the determined amino acid sequence of Petunia clone D1 and tobacco clone PROB30 is approximately 80%. PROB30 is a partial cDNA clone which corresponds with PR-protein P, an extracellular chitinase. Analyses of transgenic plants have proven that the chitinase encoded on D1 is extracellularly localized, at least in tobacco. D1 consequently contains the entire nucleotide sequence coding for an extracellular chitinase.

In order to clone the cDNA corresponding with the extracellular chitinase on a BamHI fragment, the following experiments were performed.

Two of the oligonucleotides were synthesized, namely 5'-AGCTTGGATCCGTCGACGGTCCT-3' (SEQ ID NO:1) and 5'-AATTAGGATCCGTCGACGGATCCA-3' (SEQ ID NO:2) and these were hybridized to one another, resulting in a double stranded DNA fragment with one extremity compatible with the HindIII recognition site and one extremity compatible with the EcoRI recognition site. Furthermore, the fragment contains recognition sites for BamHI, HincII and once again, BamHI. This fragment is cloned in pUC19, spliced open with EcoRI and HindIII, whereby the HindIII recognition site is restored but the EcoRI recognition site is not. The new plasmid was called pUC19+. After the extremities of the EcoRI insertion of clone D1 were filled in with Klenow polymerase according to standard techniques, the fragment was cloned into the HincII site of pUC19+.

4.2 construction of a cDNA clone coding for an entire intracellular chitinase

Screening of a new Samsun NN library (which was constructed in the same manner as the Petunia library described above) with the PROB3 insertion provided a recombinant phage. The insertion of this phage was subcloned into a plasmid as a EcoRI fragment, resulting in clone F1. Clarification of the primary structure showed that the nucleotide sequence of the insertion of F1 was identical to clone pCHN50, which was characterized by Shinshi and co-workers (1987). Because the insertion of pCHN50 has been characterized as a sequence corresponding with the intracellular chitinase of tobacco, it was concluded that the insertion of F1 also corresponds to an intracellular chitinase. The insertion of pCHN50 does not contain the entire coding sequence and is consequently incomplete. Although the insertion of F1 is 30 nucleotides longer on the 5' extremity than is pCHN50, the chitinase coding sequence contained in F1 is also incomplete.

To obtain a fragment with a sequence which codes for an entire chitinase, the following cloning steps were performed. The insertion of F1 was cloned as an EcoRI fragment into pIC19H (Marsh et al., 1984) such that the 3' extremity of the insertion properly came to the BamHI site of the polylinker. This resulted in plasmid pIC19/F1.

Two oligonucleotides were synthesized (5'-GATCCAACATGAGGCTGTGCA-3' (SEQ ID NO:3) and 5'-AATTTGCACAGCCTCATGTTG-3' (SEQ ID NO:4)) which form a fragment after hybridization to each other. This fragment is cloned in a three-point ligation reaction in a pUC plasmid spliced open with BamHI-PstI, together with the EcoRI-PstI fragment, with the 5' extremity of the open reading frame in the insertion of pIC19/F1. This cloning results in pUC/5'F1. The sequence of the oligonucleotides was chosen such that the fragment coded for five amino acids, and also such that in the eventually obtained BamHI-PstI fragment, the EcoRI recognition site was eliminated and the triplets for said five amino acids were in phase with the open reading frame in F1. After digestion of pIC19H/F1 with HindIII and (partially) with PstI, the HindIII/PstI fragment was cloned with the 3' part of the insertion into an intermediate vector lacking a EcoRI recognition site. The EcoRI site on the extremity of the insertion was replaced by filling in and back-ligation, techniques known to researchers in this area. After elimination of the EcoRI recognition site, the HindIII-PstI fragment was cloned into pUC/5'F1. The thus-obtained plasmid contains on a BamHI fragment, a cDNA with an entire coding sequence for an intracellular chitinase from tobacco. In FIG. 2, the sequence of this BamHI fragment with the deduced amino acid sequence are provided. The sequence of nucleotides 2 through 22 originates from the synthetic fragment, while nucleotides 23–27 form the remainder of the EcoRI recognition site. The PstI recognition site (5'-CTGCAG-3') is found at position 129–134. The last 21 nucleotides of this sequence successively represent a filled in EcoRI recognition site which originates from an EcoRI linker-molecule used for the construction of the cDNA library, a SmaI and a BamHI recognition site, both originating from the polylinker of pIC19H.

4.3 Construction of a gene encoding an intracellular chitinase, modified as to obtain apoplast targeting of the protein.

For the construction of a gene coding for an intracellular chitinase to be targeted to the apoplast, the sequence of the intracellular chitinase gene as shown in FIG. 2 was modified. The G at position 961 was changed into a T, hence creating a stopcodon. A second stopcodon was introduced by the replacement of the T residue at position 968 into an A. The change of the T residue at position 975 into a C resulted in the creation of a SalI-site. These modifications were introduced by using an overlapping polymerase chain reaction (PCR) technique, known to persons skilled in the art. Afterwards, the whole sequence was checked for possible introduction of mutations as a result of the PCR technique.

EXAMPLE 5

5.0 Cloning of genes coding for extra- and intracellular glucanases

The previously described lambda gt11 tobacco cDNA library was screened for recombinant phages expressing PR-2, PR-N or related sequences, with antiserum, obtained from rabbits that were immunized with tobacco PR-proteins 2 and N. The technique used was base on methods described by Huynh et al., (1985) and may be presumed to be known by researchers in this area. The insertion of one recombinant phage identified by this method, was used as a probe to rescreen the library, but this time using the plaque hybridization technique of Benton & Davis (1977). Using this method, 30 recombinant phages were identified. The insertions in the DNA of these phages were spliced open with EcoRI and subcloned into a pUC plasmid. On the basis of their various restriction patterns, the thus-obtained clones were divided into a number of groups. After subcloning in M13 vectors, the nucleotide sequences of a number of clones from each group were determined, and the amino acid sequences of the peptides encoded thereby was deduced. These analyses, in combination with the comparison of the thus-obtained sequences to sequences previously known, indicate that for at least 5 groups of clones, each codes for a unique β-1,3-glucanase. Hybridization experiments with total RNA from tobacco, whereby one of the glucanase cDNAs was used as a probe, showed that these glucanase mRNAs were also synthesized following induction with salicylate or following TMV-infection (Memelink et al., 1989).

5.1 Isolation of genes coding for extracellular β-1,3-glucanases

Using one of the above described cDNA clones, a genomic library of DNA from the nucleus of Samsun NN tobacco partially spliced with Sau3AI (Cornelissen et al., 1987), screened on recombinant phages with genes coding for glucanases. A number of recombinant phages were obtained from which four, namely gl1, gl3, gl4 and gl9 (PR-N), were further characterized. Southern blot analyses resulted in restriction maps which showed that each of the four clones contained an unique gene. After subcloning in successive pUC plasmids and M13 vectors, sequence analyses were carried out on gI3 and gI9. The sequence of the gene on clone gI9, together with the amino acid sequence deduced therefrom, are provided in FIG. 3. Comparisons teach that this amino acid sequence is identical to that of the tobacco extracellular β-1,3-glucanase PR36, the amino acid sequence of which was partially clarified (Van den Bulcke et al., 1989) with the understanding that the 21st amino acid on the C-terminal end, a threonine residue, appeared not to be present in PR36. The gene herein described is the first isolated and characterized DNA sequence coding for an extracellular β-1,3-glucanase.

To clone the gene in an expression vector, the following treatments were carried out. Using the PCR technique, known to researchers in this area, a BamHI recognition site was introduced before the gene and a HindIII recognition site was introduced after the gene. Afterwards the sequence is checked for possible introduction of mutations as a result of the PCR technique. After ligation of the gene as a BamHI-HindIII fragment into expression vector pMOG183 (see under 6), and following linearization by splicing with BamHI and HindIII, an expression unit arises on a SstI-HindIII fragment with the transcription terminator of the glucanase gene itself.

5.2 Isolation of genes coding for intracellular glucanases

A clone corresponding to an intracellular glucanase (Memelink et al., 1989) is used as a probe to search the above described genomic library. Though a large number of recombinant phages with unique insertions were obtained, it appeared after restriction analysis that only 2 unique genes are concerned. The DNA from one phage, gGLB50, was further characterized by Southern blot analysis, subcloning and via clarification of the primary structure of insertions of the relevant subclones, all of which was done using techniques known to researchers in this area. The primary structure of the gene as eventually obtained, together with the amino acid sequence deduced therefrom, are provided in FIG. 4. Comparisons teach that this amino acid sequence is extremely homologous to the sequence of an intracellular, basic β-1,3-glucanase from tobacco such as deduced from the sequences of a number of overlapping cDNA clones by Shinshi and co-workers (1988). Though the cDNAs possibly correspond to one another with strong relation, they are nevertheless different genes. At least one of the cDNA clones contains an insertion having a sequence identical to a part of the herein described gene.

To clone the gene into an expression vector, the following steps were carried out. Using the PCR technique, known by researchers in this area, a BamHI recognition site is introduced before the gene and an SstI recognition site is introduced after the gene. Afterwards, the sequence is checked for possible introduction of mutations as a result of the PCR technique. Following ligation of the gene as a BamHI-SstI fragment in expression vector pMOG185 (see under Example 6), after linearization of the vector by digestion with BamHI and SstI, an expression unit arises on a XbaI-SstI fragment with the transcription terminator of the glucanase gene itself.

In addition to the above, using the PCR technique, a BamHI recognition site is introduced before the gene. Afterwards, the sequence is checked for possible introduction of mutations as a result of the PCR technique. Subsequently, the BamHI-XbaI fragment conataining the glucanase gene was cloned into plasmid pIC19H (Marsh et al., 1984), after linearisation of the plasmid by digestion with BamHI and XbaI. After linearization of expression vector pMOG183 (see under 6) by digestion with BamHI and HindIII, the gene was ligated into this vector as a BamHI-HindIII fragment, resulting in a glucanase expression unit on a SstI-HindIII fragment with the transcription terminator of the glucanase gene itself.

5.3 Construction of a gene encoding an intracellular glucanase, modified as to obtain apoplast targeting of the protein.

For the construction of a gene coding for an intracellular glucanase to be targeted to the apoplast, modifications were made in the sequence of the intracellular glucanase gene described under 5.2. To this end the sequence GTCTCTG-GTGG (SEQ ID NO:5) (nucleotides 1883–1893 in FIG. 4) was changed into the sequence TGATATCGTTA (SEQ ID NO:6) using the PCR technique. This modification results in the introduction of two stopcodons with an EcoRV recognition site inbetween. Sequences were checked for possible introduction of mutations as a result of the PCR technique.

EXAMPLE 6

6.0 Construction of expression vectors

A high constitutive expression of genes is pending upon, inter alia, the promoter of the genes concerned. To satisfy such demands, expression vector pMOG181 was constructed, and is depicted in FIG. 5. To this end, the expression cassette of pROK1 (Baulcombe et al., 1986) is cloned in pUC18 as a EcoRI-HindIII fragment. This cassette contains the cauliflower mosaic virus (CaMV) 35S promoter on an EcoRI-BamHI restriction fragment and the nopaline synthase (nos) transcription terminator on a BamHI-HindIII fragment. The promoter fragment consists of the sequence beginning with the −800 residue and extending to and including the +1 residue of the CaMV genome, whereby position +1 is the transcription initiation site (Guilley et al., 1982). From the literature it is known that the duplication of the sequence between −343 and −90 increases the activity of the CaMV 35S promoter (Kay et al., 1987). To obtain a promoter fragment with a double so-called enhancer sequence, the following cloning steps were carried out using techniques known to researchers in this area. First, the sequence upstream from the NcoI recognition site at position −512 was deleted and the NcoI recognition site itself was changed into an EcoRI recognition site. To achieve this, the expression cassette in pUC18 was spliced open with NcoI, the thus-obtained extremities were filled in with Klenow polymerase and an EcoRI linker was ligated into the extremities. The plasmid obtained was spliced open with EcoRI, resulting in the deletion of the EcoRI fragment, and the extremities were filled in using Klenow polymerase. Afterwards, the filled in AccI-EcoRV promoter fragment (position −388 to −90) was cloned into the linear plasmid, whereby the ligation of the filled EcoRI to the filled-in AccI recognition site created a new EcoRI site. The newly obtained plasmid, pMOG181, contains the CaMV 35S promoter with double enhancer sequences in an expression cassette which still lies on an EcoRI-HindIII fragment.

Figure 6:
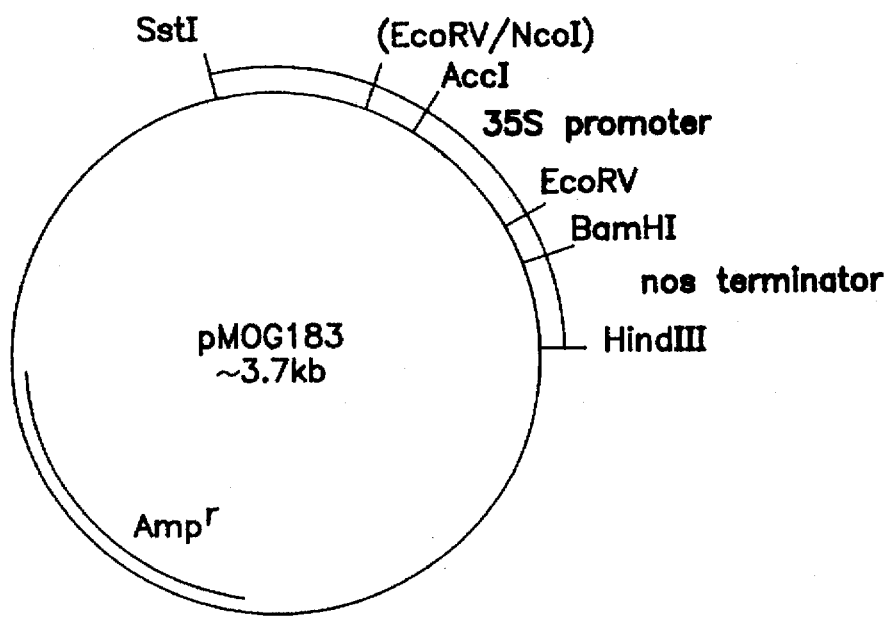
FIG. 6 shows a schematic representation of vector pMOG183, a derivate of pMOG181 wherein the EcoRI recognition site is replaced by a SstI site.
Figure 7:
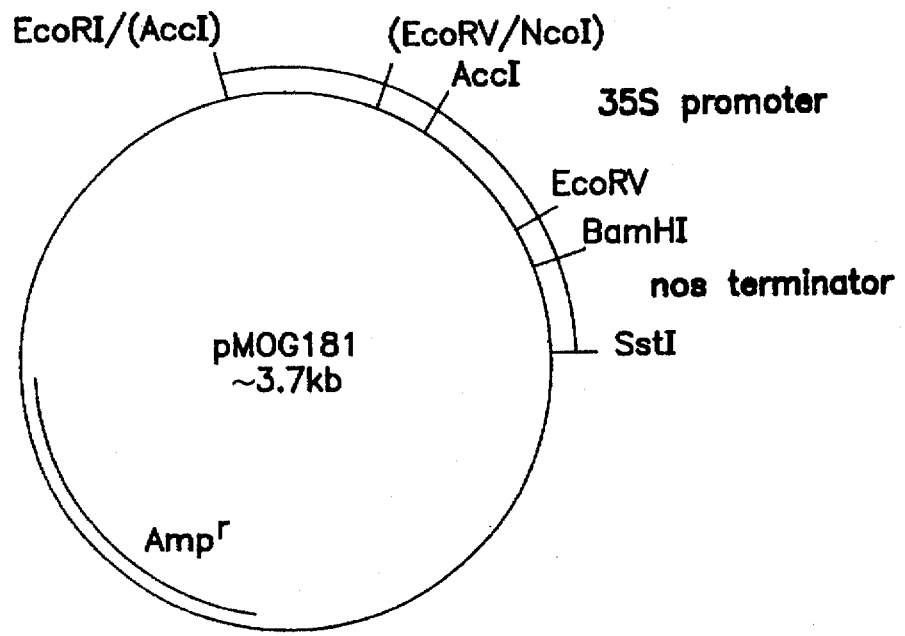
FIG. 7 shows a schematic representation of vector pMOG184, a derivative of pMOG181 wherein the HindIII recognition site is replaced by a SstI site.
Figure 8:
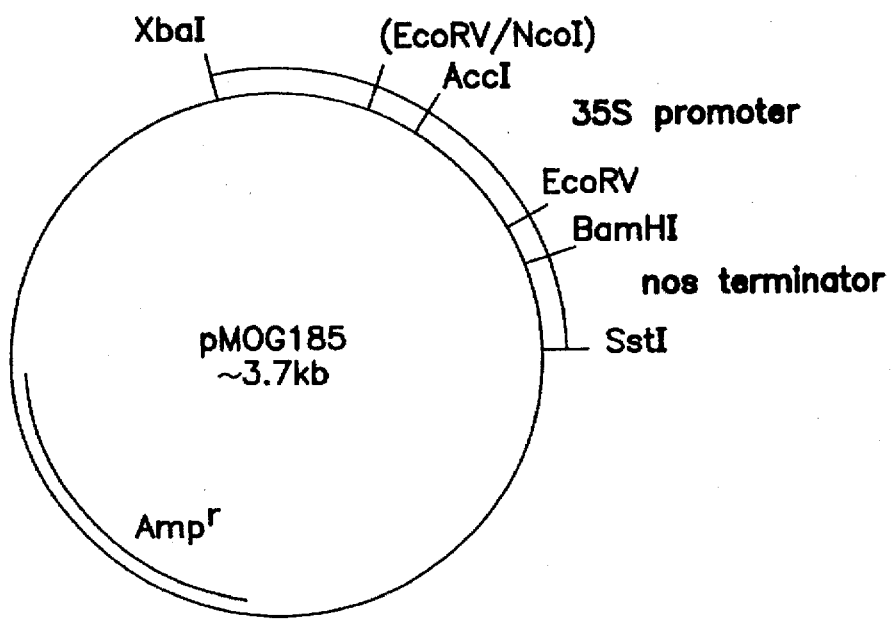
FIG. 8 shows a schematic representation of vector pMOG185, a derivate of pMOG184 wherein the EcoRI recognition site is replaced by a XbaI site.

A number of derivates were made from pMOG181. An adaptor (5'-AATTGAGCTC-3' (SEQ ID NO:7)) was cloned into the EcoRI recognition site, such that the EcoRI site was not recovered and a SstI recognition site was introduced. The resulting plasmid, pMOG183 (FIG. 6), now contains the expression cassette of a SstI-HindIII fragment. In the same manner, pMOG184 was developed from pMOG181 (FIG. 7) by the replacement of the HindIII site with a SstI recognition site. Replacement of the EcoRI site in pMOG184 by a XbaI site provided pMOG185 (FIG. 8).

EXAMPLE 7

Binary vectors

Figure 9:
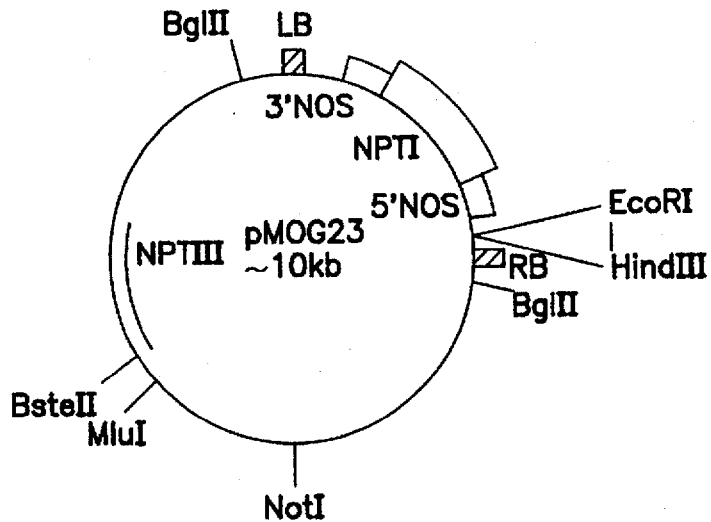
FIG. 9 (SEQ ID NO:16 and SEQ ID NO:17) shows a schematic representation of the binary vector pMOG23.
Figure 10:
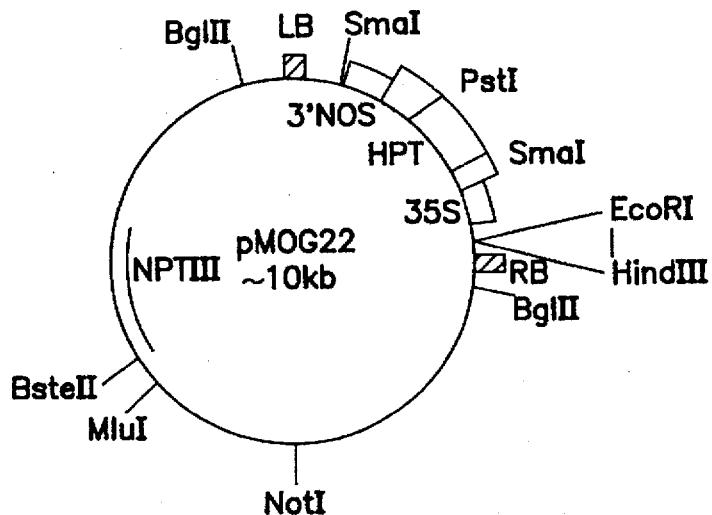
FIG. 10 shows a schematic representation of the binary vector pMOG22, a derivate of pMOG23 wherein the kanamycin resistance gene (NPTII) is replaced by a hygromycin resistance gene (HPT).

In order to introduce the chimeric chitinase and β-1,3-glucanase genes into the genome of tobacco via *Agrobacterium tumefaciens*, the binary vectors pMOG23 (FIG. 9) and pMOG22 (FIG. 10) were used. Vector pMOG23 is a derivative of vector BIN19 (Bevan, 1984). In view of this last vector, the following changes were made, which are not essential for the invention, using techniques known to researchers in this area. In the first place, the positions of the left border (LB) and the right border (RB), in view of the neomycine phosphotransferase gene II (NPTII gene), are exchanged for each other. Afterwards, the orientation of the NPTII gene is turned around such that the transcription of the gene occurs in the direction of the LB. Finally the BIN19 polylinker is replaced with a polylinker with the following restriction enzyme recognition sites: EcoRI, KpnI, SmaI, BamHI, XbaI, SacI, XhoI and HindIII.

Vector pMOG22 is a derivate of pMOG23 wherein the NPTII gene is replaced with a hygromycine resistance gene. The gene used codes for a *Escherichia coli* hygromycine phosphotransferase (HPT) and is taken from plasmid PLG90 (Van den Elzen et al., 1985). This plasmid is a derivate of pLG86 (Gritz et al., 1983) and contains a BamHI recognition site extending from 19 base pairs before the translation initiation codon to 20 base pairs after the stop codon of the gene. Using site directed mutagenesis, a standard recombinant DNA technique known to researchers in this area, the ATG codon four nucleotides before the translation initiation codon is changed into an ATA codon. In the same manner, the EcoRI recognition site in the coding region of the HPT gene is changed to 5'CAATTC 3'. Afterwards, the BamHI fragment, following filling in of both BamHI extremities using Klenow polymerase (Maniatis et al., 1982), is cloned in the BamHI recognition site of the expression cassette of pROKI (Baulcombe et al., 1986) after both BamHI extremities were also filled in. In this manner an expression unit was obtained with the HPT coding sequence between the CaMV 35S promoter and the nos transcription terminator.

EXAMPLE 8

Cloning chimeric genes in binary vectors

The cDNA coding for the extracellular chitinase (described in 4.1), the intracellular chitinase cDNA (described in 4.2) and the modified intracellular chitinase cDNA (described in 4.3) are cloned as BamHI fragments in pMOG181. Clones are selected, using restriction enzyme analysis, which had the coding sequences in the proper orientation after the promoter. Afterwards the expression cassettes isolated as EcoRI-HindIII fragments were cloned into the binary vector pMOG23, following linearisation of this plasmid this plasmid with EcoRI and HindIII . The resulting plasmids are called pMOG196, pMOG198 and pMOG189, respectively. In addition, the expression cassette with the gene encoding the intracellular chitinase modified as to target the protein to the apoplast, is cloned into pMOG22 as well, resulting in pMOG289.

The SstI-HindIII fragment with the expression unit for the intracellular glucanase modified as to target the protein to the apoplast (described in 5.3), is cloned into pMOG23, resulting in pMOG512.

Figure 11:
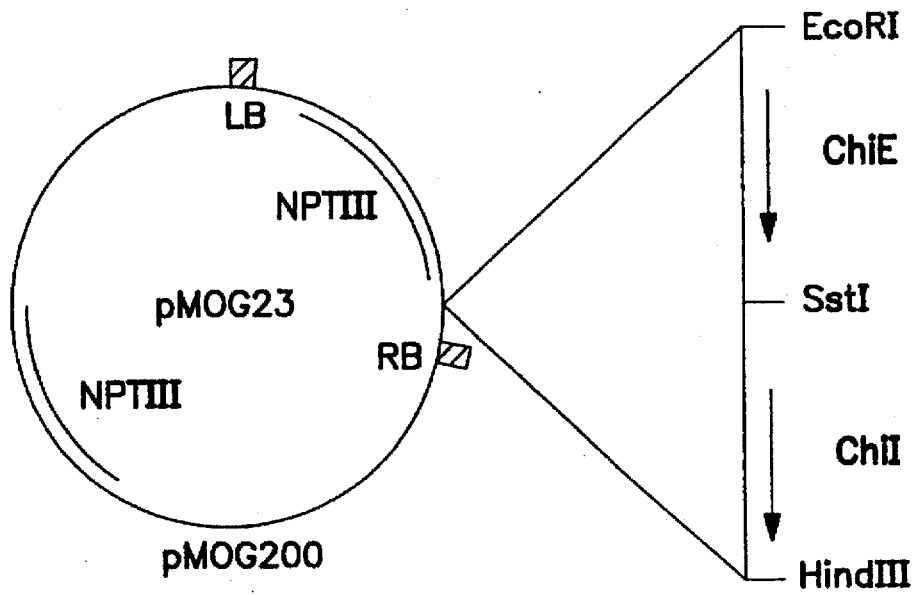
FIG. 11 shows a schematic representation of the plasmid pMOG200, a derivate of pMOG23 wherein two expression cassettes are cloned into the polylinker, viz., one with the coding sequence for an intracellular chitinase (ChiI) and one with the coding sequence for an extracellular chitinase (ChiE). The arrow provides the direction of the transcription in the cassettes, beginning with the CaMV 35S promoter.

The cDNA coding for the extracellular chitinase is cloned as a BamHI fragment in pMOG184 and the cDNA coding for the intracellular chitinase as a BamHI fragment in pMOG183. Following both cloning steps, clones are selected using restriction enzyme analysis which placed the coding sequences in the proper orientation after the promoter. Afterwards, both cassettes were isolated as EcoRI-SstI and SstI-HindIII fragments, respectively, and in a three point ligation, cloned in pMOG23, following linearization of this plasmid with EcoRI and HindIII. The plasmid obtained, pMOG200 (FIG. 11), now contains both chitinase genes on a binary plasmid physically coupled to the NPTII gene.

Figure 12:
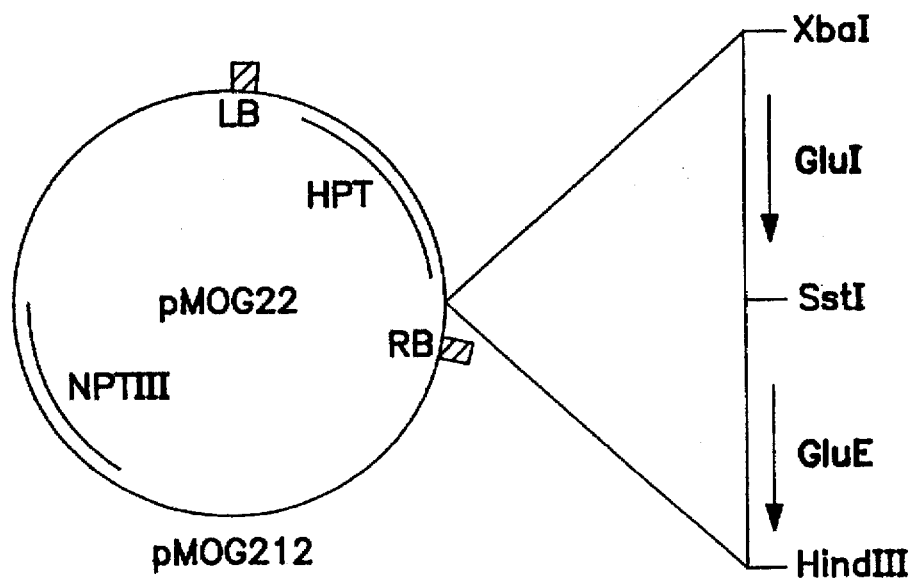
FIG. 12 shows a schematic representation of plasmid pMOG212, a derivate of pMOG22 wherein two expression cassettes are cloned into the polylinker, viz., one with the coding sequence for an extracellular β-1,3-glucanase (GluE) and one with the coding sequence for an intracellular β-1,3-glucanase (GluI). The arrows give the direction of transcription beginning with CaMV 35S promoter.

The SstI-HindIII fragment with the expression unit for the extracellular glucanase and the XbaI-SstI fragment with the expression unit before the intracellular glucanase are cloned in a three point ligation reaction into the binary vector pMOG22, following linearization of this plasmid with XbaI and HindIII. The obtained binary plasmid, pMOG212 (FIG. 12) now contains both glucanase genes physically coupled to the hygromycine resistance gene.

EXAMPLE 9

Transgenic plants

For the transformation of tobacco, use is made of leaf-discs (Horsch et al., 1985) originating from axenically cultured plants. The cultivation was performed with bacterium strains, derived from *Agrobacterium tumefaciens* strain LBA4404 (Hoekema et al., 1983) wherein a binary vector was crossed in by means of mobilisation with the help from the plasmid pRK2013 (Ditta et al., 1980). The thus-obtained Agrobacterium strains were maintained under selection pressure (20 mg/L rifampicine, 100 mg/l kanamycin), and was cultured as such for co-cultivation. The formation of transgenic shoots was established on media with 100 mg/l kanamycin in cases where derivatives of the binary vector pMOG23 were used, and on media with 20 mg/l hygromycin if derivatives of pMOG22 were used. The transgenic plants obtained from the shoots were analyzed for the expression of the newly introduced genes, using the so-called Western blotting technique. The Western blotting technique is known to researchers in this area. In some cases leaf-discs were taken from transgenic plants to insert additional genes. Kanamycin resistant leaf-discs were cocultivated with Agrobacterium strains containing pMOG22 derivatives, and hygromycin resistant leaf-discs were co-cultivated pMOG23 derivatives. The plants capable of the constitutive expression of all the introduced genes were selected, and seeds were obtained after they were fertilized via self-pollination. F1-seedlings of these transgenic plants were used for further analysis.

Transgenic tobacco plants were obtained transformed with either pMOG196, pMOG198, pMOG189 or pMOG512, and double transformed with either pMOG196+ pMOG289, pMOG512+pMOG289 or pMOG200+ pMOG212.

EXAMPLE 10

Targeting intracellular chitinase to the apoplast

To evaluate the possibility to target the intracellular chitinase to the apoplastic space, the following experiment was carried out.

Samsun NN tobacco plants were tranformed with pMOG196 to constitutively express the Petunia extracellular chitinase gene (plant line 1); with pMOG198 to constitutively express the tobacco intracellular chitinase gone (line 2); with pMOG189 to constitutively express the modified intracellular chitinase gene (line 3) and with pMOG196+ pMOG289 to constitutively express the extracellular chitinase gone and the intracellular chitinase gone modified to obtain targeting to the apoplastic space. The lines of transgenic plants were selected for high expression of each chimeric gone (up to 0.5% of total soluble protein fraction was reached). From each of the four selected lines both extracellular fluid (isolation procedure, vide: Parent & Asselin, 1984) and total leaf protein-extracts were prepared (Kaufmann et al., 1987) and these were tested for antifungal activity on the fungus *Fusarium solani*. Chitinsase activity was detected in the extracellular fluid (EF) of plant lines 1, 3, and 4, and in the total protein extract (TE) of all plant lines (1 to 4). In the antifungal assay 100 µl of EF from lines 1, 3 and 4 were added, diluted to contain a chitinase activity of approximately 2000 cpm (see example 2). The dilutions of EF of line 2, and the non-transgenic control tobacco were the same as the dilution of line 1. The 100 µl of the diluted TE of the four transgenic lines contained a chitinase activity of approximately 2000 cpm. The dilution of TE of the control was equal to that of plant line 1. The results of the antifungal assay are given in Table 2.

TABLE 2

Inhibition of growth of *Fusarium solani* by chitinases from transgenic tobacco plants

| Transgenic plant | Inhibition | |
|---|---|---|
| | Extracellular fluid | total extract |
| line 1 (extracell.) | − | − |
| line 2 (intracell.) | − | + |
| line 3 (mod. intracell.) | + | + |
| line 4 (extracell. + mod. intracellular) | + | + |
| non-transformed | − | − |

−: no inhibition; +: inhibition

Neither the EF nor the TE of line 1, expressing the Petunia extracellular chitinase gene, shows any antifungal effect, as expected from the experiments using the purified chitinases (see Example 3). The presence of chitinase activity in the EF of line 1 shows that the Petunia chitinase in tobacco is targeted to the apoplastic space.

Although in most experiments neither chitinase activity nor antifungal activity could be detected in the EF of line 2, in some experiments chitinase activity was found in the EF, probably due to leakage of the (relatively over-) expressed intracellular chitinase from the cells. The TE of line 2 showed a strong antifungal effect. Of line 3, expressing the modified apoplast-targeted intracellular chitinase gene, both the EF and the TE exhibited a strong antifungal effect. This proves that the targeted intracellular chitinase of line 3 still has antifungal activity. Apparently, deletion of (part of) the C-terminal vacuole-targeting signal does not significantly affect the antifungal activity of the intracellular chitinase.

EXAMPLE 11

Synergistic effect of glucanase on antifungal activity of chitinase

Samsun NN tobacco plants were transformed with pMOG512 to constitutively express the modified intracellular glucanase gene (line 1); with pMOG512+pMOG289 to constitutively express the modified intracellular chitinase gene and the modified intracellular glucanase gene (line 2) and with pMOG189 to express the modified intracellular chitinase gene (line 3; see example 10). The plant lines were selected for high levels of expression of each chimeric gene. From each of the selected lines extracellular fluid (EF) (Parent & Asselin, 1984) and total leaf-protein extracts (TE) (Kaufmann et al., 1987) were prepared. Initial dilutions were made of EF and TE of lines 2 and 3 to contain a chitinase activity of approximately 2000 cpm (see example 2). The initial dilutions of EF and TE of line 1 were equal to those of line 3. Subsequently, dilution series were made of the initial dilutions and these were tested for antifungal activity. No difference was found in antifungal activity between dilution series of EF and of TE. Moreover the highest antifungal activity was found in the (diluted) extracts of line 2. Apparently, the apoplast-targeted intracellular glucanase has a synergistic effect on the antifungal activity of the apoplast-targeted intracellular chitinase.

EXAMPLE 12

Analysis of transgenic plants having combined expression of an unmodified intracellular chitinase and glucanase and an extracellular chitinase and glucanase

*Phytophthora nicotianae* var. nicotianae (Pnn) is a fungus which belongs to the family of Oomycetes. It is a root pathogen of tobacco, inter alia. The infection of this plant leads to the wilting of leaves and/or to rotting in the base of the stem (black shank). Eventually the tobacco plant perishes from the infection.

To evaluate the fungal resistance of transgenic plants, that express unmodified genes encoding plant hydrolytic enzymes, the following experiment can be performed. Ten transgenic plants constitutively expressing the two unmodified chitinase and the two unmodified β-1,3-glucanase genes (unmod chitinase pmog 200; unmod gluc pmog212*), ten control plants transformed with the empty vector and ten non-transgenic plants are inoculated with a suspension in water of $2\times10^5$ Pnn zoospores. The suspension is pipetted onto the base of the stem in the soil in the pot wherein the plant is grown and thereafter rinsed with water. In the time thereafter, the plants are monitored for the development of disease symptoms. After two to three days, the control plants and the non-transgenic plants will show the first disease symptoms; after 3 weeks, approximately 17 of the 20 plants will show symptoms; a few plants will be dead. Of the transgenic plants that constitutively express the two chitinase and β-1,3-glucanase genes, just a few plants will show a slight wilting after 3 weeks.

In an alternative experiment, leaf-discs having a diameter of approximately 1 cm can obtained from the leaves of transgenic plants capable of the constitutive expression of both chitinases and both glucanases, from control transgenic plants and from non-transgenic tobacco plants. Subsequently, 10 µl of a Pnn zoospore suspension in water (5000 zoospores per ml) is pipetted onto the (underside of the) disks, and afterwards the disks are placed in sterile water and allowed to incubate at room temperature. Three sets of five disks can be used in each test, thus in total, ten control disks per experiment. The experiment can be carried a number of times with the same consistent result. After about a day, the first signs of a beginning infection will be observed on the control disks. After five days, they will be fully colonized. The disks of the transgenic plants capable of expressing chitinases and glucanases will show less severe disease symptoms, even after five days.

Tests with leaf disks, performed precisely as described above, can also performed With spores of the fungus *Thanatephorus cucumeris* (anamorph *Rhizoctonia solani* Kuhn), a basidiomycete. The inoculum concentration used can be 5000–10000 basidiospores per ml water. After ten days the disks are checked. The disks from the non-transgenic plants and the control transgenic plants will all appear to be infected, while the disks from the transgenic plants, expressing the chimeric chitinase and β-1,3-glucanase genes will be much less affected.

Likewise, the sensitivity of transgenic and control plants can be tested on the fungus *Alternaria alternata*, an Ascomycete. This fungus causes "brown-spot" in tobacco. The experiments can be performed in the manner as described by Spurr in 1973. The inoculum concentration used can be 5000–10000 conidia per ml. After 10 days, the development of "brown-spot" on the inoculated leaf material is judged according to the criteria suggested by Spurr (1973). The non-transgenic and the control leaf-material will show light to very heavy necroses, while the leaf-material having a constitutive expression of both chitinase and both β-1,3-glucanase genes will show no, or much less severe disease symptoms (light yellow lesions).

If the experiments are carried out as described above, they will show, that the constitutive expression of an extracellular chitinase and an extracellular β-1,3-glucanase and an intracellular chitinase and an intracellular β-1,3-glucanase provides a resistance against, at least a reduced susceptibility or sensitivity for fungal infections.

All publications and patent applications mentioned in this specification are indicative of the level of skill of those skilled in the art to which this invention pertains. All publications and patent applications are herein incorporated by reference to the same extent as if each individual publication or patent application was specifically and individually incorporated by reference.

Although the foregoing invention has been described in some detail by way of illustration and example for purposes of clarity of understanding, it will be obvious that certain changes and modifications may be practiced within the scope of the appended claims.

EXAMPLE 13

Figure 13:
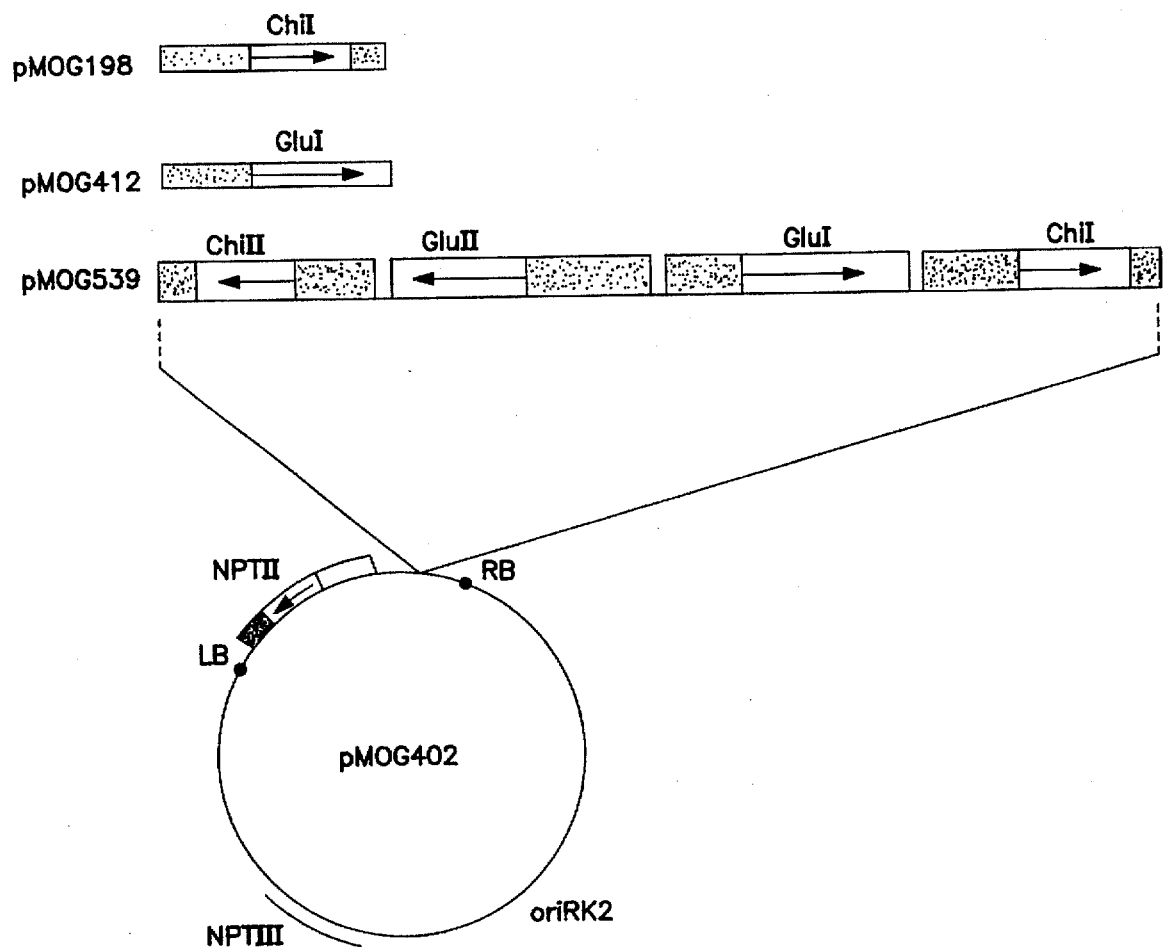
FIG. 13 is a schematic drawing of the chimeric gene constructs. Chitinase and β-1,3-glucanase genes are transcriptionally regulated by the 35S CaMV promoter (hatched box) and by the nos-terminator region (black box) or their native transcription termination signal. The arrows indicate the orientation of the respective genes. Chimeric constructs are present in the T-DNA region of binary vector pMOG402. The NPTII gene is under control of the nos-promoter (open box) and the nos-terminator region.

Chimeric gene constructs containing the cauliflower mosaic virus (CaMV) 35S promoter were made to establish the constitutive expression of tobacco chitinase and β-1,3-glucanase genes in plants. Two single-gene constructs encoding either a intracellular chitinase (32 kD) or a intracellular β-1,3-glucanase (33 kD), as well as a four-gene construct encoding both intracellular and extracellular chitinases (32 kD; PR-3a) and β-1,3-glucanases (33 kD; PR- 2b) were made by assembly of the respective genes next to the neomycin phosphotransferase II (NPTII) gene in the binary plasmid pMOG402 (FIG. 13).

The binary plasmids containing the 35S-chitinase and/or 35S-glucanase genes were constructed using a cDNA clone encoding a intracellular chitinases Chi-I (32 kD), and genomic clones encoding Chi-II (PR-3a, formerly PR-P), Glu-I (33 kD) and Glu-II (PR-2b, formerly PR-N) under control of the CaMV 35S promoter with a duplication of the enhancer region [Melchers et al., *Plant Mol Biol* (1993) 21:583]. The nos transcription terminator sequence was linked to the 3'-end of the chitinase genes, whereas the genomic glucanase constructs contained their natural terminator signals. The tailored chitinase and glucanase genes were cloned next to the chimeric NPTII gene, located between the nopaline type T-DNA border sequences of the binary plasmid pMOG402 (FIG. 1). Construct pMOG402 was derived from binary plasmid pMOG23 [Sijmons et al., *Bio/Technology* (1990) 8:217] by substitution of the wild-type NPTII coding region for the mutant NPTII coding region [Yenofsky et al., *Proc Natl Acad Sci USA* (1990) 87:3435] of pMOG23.

The chimeric constructs were mobilized from *Escherichia coli* DH5α into *Agrobacterium tumefaciens* strain MOG101 and used to infect cotyledon explants of tomato, *Lycopersicon esculentum* cv Moneymaker. The kanamycin-resistant (Km$^r$) primary transformants were grown in the greenhouse and screened for ploidy level.

The diploid kanamycin-resistant primary transformants were selected by counting similar chloroplasts of the stomatal guard cells [Koorneef et al., *Euphitica* (1989) 43:179].

Diploid tomato plants constitutively expressing tobacco chitinase and/or β-1,3-glucanase genes showed no obvious aberrant phenotype when compared to wild-type or transgenic vector control plants. Km$^r$-progeny plants obtained from selfing were used to determine the number of T-DNA loci in each line and were analyzed for the expression level of the chitinase and β-1,3-glucanase genes.

Transgenic tomato lines were selfpolinated and the S1-progeny was analyzed for the number of T-DNA loci present on the basis of segregation for kanamycin-resistance, using a non-destructive spraying assay [Weide et al., *Theor Appl Genet* (1989) 78:169].

Protein expression levels were quantified by immunoblot analysis using a concentration range (12.5, 25, 50 and 100 ng) of purified chitinases (PR-3a; 32 kD Chi-I) and glucanases (PR-2b; 33 kD Glu-1) as a standard (5). Mean expression levels were determined in S1-plants, prior to infection with *F. oxysporum*. Soluble protein fractions (5 μg), isolated from a mixed leaf sample of 7 kanamycin resistant plants, were fractionated by 10% SDS-polyacrylamide gel electrophoresis and analyzed on Western blots as described by Melchers et al., *Plant Mol Biol* (1993) 21:583. Antibodies raised against PR-3a (Chi-II) (detection of both Chi-I and Chi-II proteins), Glu-I and PR-2b (Glu-II) were used in a $10^4$-fold dilution except for antiserum to Glu-I ($2.10^3$-fold dilution).

The expression levels of the chitinase and β-1,3-glucanase proteins varied from 0 to 4% of total soluble protein, except for Chi-II expression which appeared to be low and often undetectable.

Transgenic plants were assayed for resistance to the phytopathogen *F. oxysporum* f.sp. lycopersici race 1, a soil-borne fungus that infects the vascular tissue of tomato after penetration of roots through wound sites. Characteristic disease symptoms observed in tomato plants after infection with *F. oxysporum* f.sp. lycopersici are adventitious root formation, wilting followed by chlorosis and necrosis of leaves, resulting eventually in death of the plant. S1-progeny was tested for resistance to *F. oxysporum* in randomized complete block experiments with 3 replicates and 7 plants per plot. The severity of the disease symptoms was scored 25 to 30 days post-infection using a graduated disease scale.

Fusarium resistance in tomato was tested using 25 days old tomato S1-seedlings selected for kanamycin resistance, including hemizygous and homozygous plants. All plant lines were tested in three randomized complete block experiments with 3 replicates and 7 plants per plot. Plants were inoculated by dipping the roots (rinsed with water) in a *Fusarium oxysporum* f.sp. lycopersici race 1 inoculum of $10^6$ micro-conidia/mL. The inoculum was prepared from fungal mycelia freshly grown on potato dextrose agar plates for 25 days at 18° C. and 18 hours light (8 Lux). Growth conditions for inoculated plants were 80% relative humidity, 18° C. and 15 house light period (40 Lux). Disease symptoms were scored 25 to 30 days post inoculation by the time Moneymaker control plants had developed severe wilting and chlorosis. Plants were cut longitudinally at the stem base and scored using the following severity scale: 0, no symptoms; 1, slight browning of vascular tissue, no wilting of leaves; 3, browning of vascular tissue and wilting of leaves; 5, browning of vascular tissue, wilting of leaves and some chlorosis; 7, severe wilting and chlorosis of leaves; 9, necrosis, dead plant. For each transgenic line mean levels of disease severity per plot (7 plants) were calculated and compared by 'Oneway Analysis of Variance' according to Duncan's multiple range procedure.

Transgenic tomato plants expressing constitutively only one antifungal gene, either a class I chitinase or β-1,3-glucanase, showed no increased resistance to *F. oxysporum* (Table 3). One tomato line (MM-412-04) showed an enhanced resistance compared to the wild-type Moneymaker, but did not significantly differ from the fully susceptible vector control plants (MM-402-09). The slightly enhanced resistance (32.2% reduction in disease rating) of this tomato Glu-I line might be due to the fact that in addition to the constitutive expression of the β-1,3-glucanase transgene, expression of an endogenous tomato chitinase gene was induced (Table 3).

The influence of the simultaneous expression of chitinase and β-1,3-glucanase genes on Fusarium resistance of tomato was tested using plants containing the four-gene construct (pMOG539) (Table 4). Between the twelve transgenic lines containing this construct considerable variation in disease severity was observed. As expected, disease symptoms were consistently absent in control cultivars with host gene mediated immunity to *F. oxysporum* f.sp. lycopersici race 1 (Belmondo and Dombito) and in non-inoculated wild-type Moneymaker. Similarly, the disease severity observed in fully susceptible control cultivars (Planet and Moneymaker) did not significantly differ from that observed in the empty vector control (MM-402-09). This indicates that expression of the NPTII gene did not affect Fusarium resistance. Seven transgenic lines proved significantly more resistant and five were essentially as sensitive as control plants to Fusarium infection (Table 4). The reduction in disease severity rating in the resistant lines ranged from 36.3% (MM-539-16) up to 57.8% (MM-539-61) and was confirmed (50.9% up to 84.4% reduction) in a second experiment (data not shown). Transgenic lines MM-539-18 and MM-539-61 were shown to largely recover from Fusarium infection by the time wild-type Moneymaker had died.

To establish to what extent the intracellular and extracellular chitinases and β-1,3-glucanase contributed to resistance in the four-gene transgenic lines, the correlation between mean expression levels and disease severity was analyzed. These analyses demonstrated that enhanced levels of Fusarium resistance observed in transgenic tomato lines containing the four-gene construct largely resulted from the simultaneous expression of both the tobacco intracellular chitinase and extracellular β-1,3-glucanase gene. Firstly, because high expression of both chitinase and β-1,3-glucanase genes coincided with lower disease severity (Pearson correlation coefficients of −0.77 ($P<0.01$) and −0.54 ($P<0.05$), respectively), whereas the extracellular β-1,3-glucanase expression level did not (Pearson correlation coefficient 0.22 ($P>0.05$). Secondly, simultaneous expression of Chi-I (1.5–4%) and Glu-I (0.1–2%) resulted in a significant enhanced disease resistance, while similar expression levels of either Chi-I or Glu-I alone did not. In addition, our data suggest that the intracellular β-1,3-glucanases did not play a pivotal role in the observed increased resistance to Fusarium in the lines tested. Since the expression level of the extracellular chitinase gene was low, the role of Chi-II proteins in disease resistance remains unclear.

TABLE 3

Disease severity of tomatoe S1-lines transgenic for a single chitinase or β-1,3-glucanase construct inoculated with *F. oxysporum* f.sp. lycopersici race 1.
Mean chitinase and β-1,3-glucanase protein expression levels and the number of T-DNA loci present, are shown for each plant line.

| Cultivars* | Construct Gene | Loci | Disease severity$ Mean | σ | Expression levels* Chi-I | Glu-I |
|---|---|---|---|---|---|---|
| Non-Inoculated: | | | | | | |
| Moneymaker (MM) | — | — | 0.00 a | 0.00 | 0 | 0 |
| Inoculated: | | | | | | |
| MM-412-04 | Glu-1 | 1 | 4.94 b | 1.58 | 1.0⁺ | 0.75 |
| MM-412-03 | Glu-I | 1 | 5.38 bcd | 1.01 | 0 | 0.75 |
| MM-402-09 | — | 1 | 6.14 bcd | 0.52 | 0 | 0 |
| MM-412-06 | Glu-I | 1 | 6.38 bcd | 0.80 | 0 | 1.5 |
| MM-412-02 | Glu-I | 1 | 6.67 cd | 0.91 | 0 | 1.5 |
| MM-198-02 | Chi-I | 1 | 7.21 d | 0.13 | 4.0 | 0 |
| Moneymaker (MM) | — | — | 7.29 d | 0.14 | 0 | 0 |
| MM-198-01 | Chi-I | 2 | 7.48 d | 0.52 | 4.0 | 0 |

*Protein expression level as percentage of the total soluble protein of a tomato leaf extract. None of the plants showed expression of Chi-II or Glu-II.
$Disease severity scored 26 days post-inoculation. Different letters indicate significant differences in disease severity according to Duncan's multiple range test (α = 0.05).
&Cultivar numbers refer to the constructs shown in FIG. 1.
⁺Induced expression of an endogenous tomato chitinase gene.

TABLE 4

Disease severity of tomato S1-lines transgenic for a four-gene chitinase and β-1,3-glucanase construct inoculated with *F. oxysporum* f.sp. lycopersici race 1. Mean chitinase and β-1,3-glucanase protein expression levels and the number of T-DNA loci present, are shown for each plant line.

| Cultivars* | Construct Genes | Loci | Disease severity$ Mean | σ | Expression levels* Chi-I | Chi-II | Glu-I | Glu-II |
|---|---|---|---|---|---|---|---|---|
| Non-inoculated: | | | | | | | | |
| Moneymaker (MM) | — | — | 0.00 a | 0.00 | 0 | 0 | 0 | 0 |
| Inoculated: | | | | | | | | |
| Belmondo | — | — | 0.00 a | 0.00 | 0 | 0 | 0 | 0 |

TABLE 4-continued

Disease severity of tomato S1-lines transgenic for a four-gene chitinase
and β-1,3-glucanase construct inoculated with
F. oxysporum f.sp. lycopersici
race 1. Mean chitinase and β-1,3-glucanase protein expression levels
and the number of T-DNA loci present, are shown for each plant line.

| Cultivars[&] | Construct Genes | Loci | Disease severity[$] Mean | σ | Expression levels[*] Chi-I | Chi-II | Glu-I | Glu-II |
|---|---|---|---|---|---|---|---|---|
| Dombito | — | — | 0.00 a | 0.00 | 0 | 0 | 0 | 0 |
| MM-539-61 | Chi-I,II/Glu-I,II | 1 | 2.90 b | 0.46 | 2.0 | 0 | 1.0 | 2.0 |
| MM-539-18 | Chi-I,II/Glu-I,II | 1 | 3.05 b | 0.67 | 4.0 | 0.05 | 1.5 | 2.0 |
| MM-539-51 | Chi-I,II/Glu-I,II | ? | 3.19 bc | 0.97 | 4.0 | 0 | 1.0 | 3.0 |
| MM-539-31 | Chi-I,II/Glu-I,II | 1 | 3.52 bcd | 0.71 | 1.5 | 0 | 2.0 | 3.0 |
| MM-539-10 | Chi-I,II/Glu-I,II | 1 | 3.66 bcd | 1.00 | 4.0 | 0.1 | 0.1 | 0 |
| MM-539-20 | Chi-I,II/Glu-I,II | 2 | 3.86 bcde | 1.51 | 1.5 | 0.05 | 1.0 | 3.0 |
| MM-539-16 | Chi-I,II/Glu-I,II | ? | 4.38 bcde | 1.58 | 4.0 | 0.1 | 0.1 | 0 |
| MM-539-19 | Chi-I,II/Glu-I,II | 1 | 4.95 cdef | 1.64 | 1.0 | 0.05 | 1.0 | 3.0 |
| MM-539-60 | Chi-I,II/Glu-I,II | 1 | 5.24 defg | 1.62 | 0.5 | 0 | 1.0 | 1.0 |
| MM-539-34 | Chi-I,II/Glu-I,II | ? | 5.34 defg | 1.28 | 1.0 | 0 | 1.0 | 0 |
| MM-539-02 | Chi-I,II/Glu-I,II | 1 | 5.63 efg | 0.67 | 0.5 | 0 | 1.0 | 3.0 |
| MM-402-09 | — | 1 | 6.45 fg | 0.04 | 0 | 0 | 0 | 0 |
| MM-539-50 | Chi-I,II/Glu-I,II | 1 | 6.67 fg | 1.53 | 0.5 | 0 | 0.5 | 3.0 |
| Moneymaker (MM) | — | — | 6.88 g | 1.12 | 0 | 0 | 0 | 0 |
| Planet | — | — | 6.91 g | 0.44 | 0 | 0 | 0 | 0 |

[&]Moneymaker (MM) and Planet are susceptible cultivars, whereas Belmondo and Dombito possess host-gene immunity to F. oxysporum f.sp. lycopersici race 1.
? unknown, since a 1:1 segregation for Km resistance was found.
[$]Disease severity scored 30 days post-inoculation.
See also legend to Table 1.

DEPOSIT OF MICROORGANISMS

The *Escherichia coli* strain DH5α, containing the plasmid pMOG23 (CBS 102.90) and the *Escherichia coli* strain DH5α containing the plasmid pMOG22 (CBS 101.90) were deposited on Jan. 29, 1990, at the Centraal Bureau voor Schimmelcultures (CBS), Baarn, the Netherlands. The genotype of *Escherichia coli* strain DH5α is: F⁻, endA1, hsdR17 ($r_k$ m $m_k^+$), supE44, thi-1, lambda⁻, recA1, gyrA96, relA1, φ80dlacZ M15.

The *Agrobacterium tumefaciens* strain LBA4404, which is a good acceptor strain for all binary plant transformation vectors, has been previously deposited on Feb. 24, 1983 and is available via the Centraal Bureau voor Schimmelcultures, Baarn, the Netherlands, under number CBS 191.83.

REFERENCES

Abeles, F. B., Bosschart, R. P., Forrence, L. E. & Habig, W. H. (1971), Plant Physiol. 47, 129–134.

Ballance, G. M., Meredith, W. O. S., & Laberge, D. E. (1976), Can. J. Plant Sci. 56, 459–466.

Baulcombe, D. C., Saunders, G. R., Bevan, M. W., Mayo, M. A. & Harrison, B. D. (1986), Nature 321, 446–449.

Bauw, G., De Loose, M., Inzé, D., Van Montagu, M. & Vandekerckhove, J. (1987), Proc. Natl. Acad. Sci. USA 84, 4806–4810.

Bell, J. N., Ryder, T. B., Wingate, V. P. M., Bailey, J. A. & Lamb, C. J. (1986), Mol. Cell. Biol. 6, 1615–1523.

Benton, W. D. & Davis, R. W. (1977), Science 196, 180–182.

Bevan, M. (1984), Nucl. Acids Res. 22, 8711–8721.

Boller, T., Gehri, A., Mauch, F. & Vögeli, U. (1983), Planta 157, 22–31.

Boller, T. & Métraux, J. P. (1988), Mol. Plant Pathol. 33, 11–16.

Boller, T. & Vögeli, U. (1984), Plant Physiol. 74, 442–444.

Broglie, K. E., Gaynor, J. J. & Broglie, R. M. (1986), Proc. Natl. Acad. Sci. USA 83, 6820–6824.

Broglie, K. E., Biddle, P., Cressman, R. & Broglie, R. M. (1989), Plant Cell 1, 599–607.

Chappell, J., Hahlbrock, & Boller, T. (1984), Planta 161, 475–480.

Christ, U. & Mösinger, E. (1989), Physiol. Mol. Plant Pathol. 35, 53–65.

Cohen, Y. & Kuc, J. (1981), Phytopathology 71, 783–787.

Cornelissen, B. J. C., Horowitz, J., Van Kan, J. A. L., Goldberg, R. B. & Bol, J. F. (1987), Nucl. Acids Res. 15, 6799–6811.

Cramer, C. L., Bell, J. N., Ryder, T. B., Bailey, J. A., Schuch, W., Bolwell, G. P., Robbins, M. P., Dixon, R. A. & Lamb, C. J. (1985), EMBO J. 4, 285–289.

Cruickshank, I. A. M. & Mandryk, M. (1960), Aust. Inst. Agric. Sci. 26, 369–372.

Darvill, A. G. & Albertsheim, P. (1984), Plant Physiol. 35, 243–275.

De Loose, M., Alliotte, T., Gheysen, G., Genetello, C., Gielen, J., Soetaert, P., Van Montagu, M. & Inzé, D. (1988), Gene 70, 13–23.

De Wit, P. J. G. M., Buurlage, M. B. & Hammond, K. E. (1986), Physiol. Mol. Plant Pathol. 29, 159–172.

De Wit, P. J. G. M. & Van der Meer, F. E. (1986), Physiol. Mol. Plant Pathol. 28, 203–214.

Ditta, G., Stanfield, S., Corbiu, D. & Helinski, D. (1980), Proc. Acad. Natl. Sci. USA 77, 7347–7351.

Elliston, J., Kuc, J. & Williams, E. B. (1977), phytopathol. Z. 87, 289–303.

Felix, G. & Meins, F. (1985), Planta 164, 423–428.

Felix, G. & Meins, F. (1986), Planta 167, 206–211.

Felix, G. & Meins, F. (1987), Planta 172, 386–392.

Ferraris, L., Abbattista Gentile, I. & Matta, A. (1987), J. Phytopathol. 118, 317–325.

Fincher, G. B., Lock, P. A., Morgan, M. M., Lingelbach, K., Wettenhall, R. E. H., Mercer, J. F. B., Brandt, A. & Thomsen, K. K. (1986), Proc. Natl. Acad. Sci. USA 83, 2081–2085.

Fink, W., Liefland, M. & Mendgen, K. (1988), Plant Physiol. 88, 270–275.

Fischer, W., Christ, U., Baumgartner, M., Erismann, K. H. & Mösinger, E. (1989), Physiol. Mol. Plant Pathol. 35, 67–83.

Fortin, M. G., Parent, J-G. & Asselin, A. (1985), Can. J. Bot. 63, 932–937.

Gaynor, J. J. (1988), Nucl. Acids Res. 16, 5210.

Gessler, G. & Kuc, J. (1982), J. Exp. Bot. 33, 58–66.

Gilpatrick, J. D. & Weintraub, M. (1952), Science 115, 701–702.

Guilley, H., Dudley, R. K., Jonard, G., Balazs, E. & Richards, K. E. (1982), Cell 30, 763–773.

Gritz, L. & Davies, J. (1983), Gene 25, 179–188.

Hadwiger, L. A. & Beckman, J. A. (1980), Plant Physiol. 66, 205–211.

Hecht, E. I. & Bateman D. F. (1964), Phytopathology 54, 523–530.

Hedrick, S. A., Bell, J. N., Boller, T. & Lamb, C. J. (1988), Plant Physiol. 86, 182–186.

Hilborn, M. T. & Farr, W. K. (1959), Phytopath. 70, 35–39.

Hoekema, A., Hirsch, P. R., Hooykaas, P. J. J. & Schilperoort, R. A. (1983), Nature 303, 179–180.

Hoj, P. B., Hartman, D. J., Morrice, N. A., Doan, D. N. P. & Fincher, G. B. (1989), Plant Mol. Biol. 13, 31–42.

Hoj, P. B., Macauly, B. J. & Fincher, G. B. (1981), J. Inst. Brew. 87, 77–80.

Hoj, P. B., Slade, A. M., Wettenhall, R. E. H. & Fincher, G. B. (1988), FEBS Lett. 230, 67–71.

Hooft van Huijsduijnen, R. A. M., Van Loon, L. C. & Bol, J. F. (1986), EMBO J. 5, 2057–2061.

Hooft van Huijsduijnen, R. A. M., Kauffmann, S., Brederode, F. Th., Cornelissen, B. J. C., Legrand, M., Fritig, B. & Bol, J. F. (1987), Plant Mol. Biol. 9, 411–420.

Horsch, R. B., Fry, J. E., Hoffmann, N., Wallroth, M., Eichholz, D., Rogers, S. G. & Fraley, R. T. (1985), Science 227, 1229–1231.

Hunsley, D. & Burnett, J. H. (1970), J. Gen. Microbiol. 62, 203–218.

Jamet, E. & Fritig, B. (1986), Plant Mol. Biol. 6, 69–80.

Jones, D., Gordon, A. H. & Bacon, J. S. D. (1974), Biochem. J. 140, 47–55.

Joosten, M. H. A. & De Wit, P. J. G. M. (1989), Plant Physiol. 89, 945–951.

Kauffmann, S., Legrand, M., Geoffroy, P. & Fritig, B. (1987), EMBO J. 6, 3209–3212.

Kay, R., Chan, A., Daly, M. & McPherson, J. (1987), Science 236, 1299–1302.

Keen, N. T. & Yoshikawa, M. (1983), Plant Physiol. 71, 460–465.

Kombrink, E. & Hahlbrock, K. (1986), Plant Physiol. 81, 216–221.

Kombrink, E., Schröder, M. & Hahlbrock, K. (1988), Proc. Natl. Acad. Sci. USA 85, 782–786.

Kuc, J. (1982), Wood, R. K. S. ed pp. 157–178. Plenum Press, New York.

Leah, R., Mikkelsen, J. D., Mundy, J. & Svendsen, I. (1987), Carlsberg Res. Commun. 52, 31–37.

Laflamme, D. & Roxby, R. (1989), Plant Mol. Biol. 13, 249–250.

Legrand, M., Kauffmann, S., Geoffroy, P. & Fritig, B. (1987), Proc. Natl. Acad. Sci. USA 84, 6750–6754.

Lotan, T., Ori, N. & Fluhr, R. (1989), Plant Cell 1, 881–887.

Mandryk, M. (1963), Adam. Aust. J. Agric. Res. 14, 315–318.

Maniatis, T., Fritsch, E. F. & Sambrook, J. (1982), Cold Spring Harbor Laboratory, CSH, New York.

Marsh, J. L., Erfle, M. & Wykes, E. J. (1984), Gene 32, 481–485.

Mauch, F., Hadwiger, L. A. & Boller, T. (1984), Plant Physiol. 76, 607–611.

Mauch, F., Hadwiger, L. A. & Boller, T. (1988a), Plant Physiol. 87, 325–333.

Mauch, F., Mauch-Mani, B. & Boller, T. (1988b), Plant Physiol. 88, 936–942.

Mauch, F. & Staehelin, L. A. (1989), Plant-Cell 1, 447–457.

Mazau, D. & Esquerré-Tugayé, M. T. (1986), Physiol. Mol. Plant Pathol. 29, 147–157.

McIntyre, J. R. & Dodds, J. A. (1979), Physiol. Plant Pathol. 15, 321–330.

McIntyre, J. L., Dodds, J. A. & Hare, J. D. (1981), Phytopathology 71, 297–301.

Meins, F. & Ahl, P. (1989), Plant Science 61, 155–161.

Memelink, J., Hoge, J. H. C. & Schilperoort, R. A. (1987), EMBO J. 6, 3579–3583.

Memelink, J., Linthorst, H. J. M., Schilperoort, R. A. & Hoge, J. H. C. (1989), Plant Mol. Biol. ter perse.

Métraux, J. P. & Boller, T. (1986), Physiol. Mol. Plant Pathol. 28, 161–169.

Métraux, J. P., Streit, L. & Staub, T. (1988), Physiol. Mol. Plant Pathol. 33, 1–9.

Métraux, J. P., Burkhart, W., Moyer, M., Dincher, S., Middlesteadt, W., Williams, S., Payne, G., Carnes, M. & Ryals, J. (1989), Proc. Natl. Acad. Sci. USA 86, 896–900.

Mohnen, D., Shinshi, H., Felix, G. & Meins, F. (1985), EMBO J. 4, 1631–1635.

Molano, J., Duran, A. and Cabib, E. (1977) Chitin. Anal. Biochem. 83, 648–656.

Moore, A. E. & Stone, B. A. (1972), Virology 50, 791–798.

Nasser, W., De Tapia, M., Kauffmann, S., Montasser-Kouhsari., S. & Burkard, G. (1988), Plant Mol. Biol. 11, 529–538.

Parent, J. G. & Asselin, A. (1984), Can. J. Bot. 62, 564–569.

Pegg, G. F. & Young, D. H. (1981), Physiol. Plant Pathol. 19, 371–382.

Pegg, G. F. & Young, D. H. (1982), Physiol. Plant Pathol. 21, 89–409.

Ross, A. F. (1961), Virology 14, 340–358.

Ross, A. F. & Bozarth, R. F. (1960), Phytopathology 50, 652.

Sanger, F., Nicklen, S. & Coulson, A. R. (1977), Proc. Natl. Acad. Sci. USA 74, 5463–5467.

Schlumbaum, A., Mauch, F., Vögeli, U. & Boller, T. (1986), Nature 324, 365–367.

Sequeira, L. (1983), Ann. Rev. Microbiol. 37, 51–79.

Shinshi, H., Mohnen, D. & Meins, F. (1987), Proc. Natl. Acad. Sci. USA 84, 89–93.

Shinshi, H., Wenzler, H., Neuhaus, J-M., Felix, G., Hofsteenge, J. & Meins, F. (1988), Proc. Natl. Acad. Sci. USA 85, 5541–5545.

Showalter, A. M., Bell, J. N., Cramer, C. L., Bailey, J. A., Varner, J. E. & Lamb, C. J. (1985), Proc. Natl. Acad. Sci. USA 82, 6551–6555.

Skujins, J. J., Potgieter, H. J. & Alexender, M. (1965), Arch. Biochem. Biophys. 111, 358–364.

Spanu, P., Boller, T., Ludwig, A., Wiemken, A., Faccio, A. & Bonfante-Fasolo, P. (1989), Planta 177, 447–455.

Stuart, I. M., Loi, L. & Fincher, G. B. (1986), Plant Physiol. 80, 310–314.

Swegle, M., Huang, J-K., Lee, G. & Muthukrihnan, S. (1989), Plant Mol. Biol. 12, 403–412.

Toppan, A. & Esquerré-Tugayé, M. T., (1984), Plant Physiol. 75, 1133–1138.

Van den Bulcke, M., Bauw, G., Castresana, C., Van Montegu, M. & Vandekerckhove, J. (1989), Proc. Natl. Acad. Sci. USA 86, 2673–2677.

Van den Elzen, P. J. M., Towsend, J., Lee, K. Y. & Bedbrook, J. R. (1985), Plant Mol. Biol. 5, 299–302.

Van Loon, L. C. (1975), Virology 67, 566–575.

Van Loon, L. C. & Antoniw, J. F. (1982), Neth. J. Plant Pathol. 88, 237–256.

Vögeli, U., Meins, F. & Boller, T. (1988), Planta 174, 364–372.

Vögeli-Lange, R., Hansen-Gehri, A., Boller, T. & Meins, F. (1988), Plant Science 54, 171–176.

Wargo, P. M. (1975), Physiol. Plant Pathol. 5, 99–105.

Wessels, J. G. H. & Sietsma, J. H. (1981), Encyclopedia of Plant Physiology, N.S., vol. 13B: Plant Carbohydrates II. pp. 352–394, Tanner, W., Loewus, F. A., eds. Springer, Berlin, Heidelberg, New York.

Woodward, J. R. & Fincher, G. B. (1982), Eur. J. Biochem. 121, 663–669.

Woodward, J. R., Morgan, F. J. & Fincher, G. B. (1982), FEBS Lett. 138, 198–200.

Young, D. H. & Pegg, G. P. (1981), Physiol. Plant Pathol. 21, 391–417.

Young, D. H. & Pegg, G. P. (1982), Physiol. Plant Pathol. 21, 411–423.

---

We claim:

1. A transgenic plant that has been transformed with and expresses an intracellular plant chitinase gene and a plant β-1,3-glucanase gene in at least one of the plant tissues.

2. The plant of claim 1 wherein the β-1,3-glucanase is an intracellular glucanase and wherein the intracellular chitinase and the intracellular β-1,3-glucanase are targeted to the apoplast by virtue of modification at the C-terminus thereof.

3. The plant of claim 2 wherein the gene encoding the intracellular β-1,3-glucanase gene is modified by creating a translation stop codon in the coding region at the 3' end of the gene.

4. The plant of claim 3 wherein creation of the translation stop codon results in deletion of between 3 and 25 C-terminal amino acids of said intracellular β-1,3-glucanase.

5. A plant according to claim 1, wherein the newly introduced genes are under the control of the CaMV 35S promoter.

6. Plasmid pMOG200, or a derivative thereof.

7. Plasmid pMOG212, or a derivative thereof.

8. Plasmid pMOG512, or a derivative thereof.

9. Agrobacterium strains harboring the plasmid of claim 6.

10. Agrobacterium strains harboring the plasmid of claim 7.

11. Agrobacterium strains harboring the plasmid of claim 8.

12. A process for obtaining fungal resistant plants by introducing into the genome of said plants, or their ancestors, or any plant part that can be regenerated to produce said plant, the recombinant polynucleotide of claim 11.

13. A plant comprising a recombinant plant genome which genome has been modified so as to include a first expression system for an intracellular plant chitinase and a second expression system for an intracellular plant β-1,3-glucanase which when expressed in said plant exhibit a synergistic antifungal effect.

14. The plant of claim 13 wherein said antifungal effect is with respect to *Fusarium oxysporium* f.sp. Lycopersice.

15. The plant of claim 13 wherein at least one of said chitinase and glucanase is modified at the C-terminus to effect its secretion into the apoplastic space.

16. A recombinant plant which exhibits, as a result of expression of one or more recombinant polynucleotides encoding an intracellular plant chitinase and a β-1,3-glucanase, a relative overexpression of said chitinase and glucanase relative to a plant of the same line that does not express said one or more recombinant polynucleotides, wherein said chitinase and glucanase in combination exhibit a synergistic antifungal effect in the plant.

17. The plant of claim 16 wherein said antifungal effect is with respect to *Fusarium oxysporium* f.sp. Lycopersice.

18. The plant of claim 16 wherein at least one of said first and second proteins is modified at the C-terminus to effect its secretion into the apoplastic space.

19. The plant of claim 1 wherein the chitinase is an intracellular chitinase and wherein the intracellular chitinase is targeted to the apoplast by virtue of modification at the C-terminus thereof.

20. The plant of claim 19 wherein the gene encoding the intracellular chitinase is modified by creating a stop codon in the coding region at the 3' end of the gene.

21. The plant of claim 20 wherein creation of the translation stop codon results in deletion of between 3 and 10 C-terminal amino acids of said intracellular chitinase.

22. A recombinant polynucleotide comprising genetic information for the relative overexpression, relative to a plant of the same line that does not express said recombinant polynucleotide, of a first gene encoding an intracellular plant chitinase and a second gene encoding a β-1,3-glucanase wherein said chitinase and glucanase, when produced in combination, exhibit a synergistic antipathogenic effect in said plant, which polynucleotide comprises:

(a) a first promoter that is functional in plants, (b) said first gene under control of said first promoter, (c) a terminator operably linked to said first gene; and (d) a second promoter that is functional in plants, (e) said second gene under control of said second promoter, (f) a terminator operably linked to said second gene; and, optionally, (g) a gene encoding a selectable or screenable trait, operably linked to regulatory sequences for proper expression.

23. The polynucleotide of claim 22 wherein said intracellular chitinase gene is modified by creating a translation stop codon in the coding region at the 3' end of the gene.

24. The polynucleotide of claim 23 wherein the gene encoding the intracellular β-1,3-glucanase is modified by creating a translation stop codon in the coding region at the 3' end of the gene.

25. Agrobacterium strains modified to contain the polynucleotide of claim 22.

26. The plant according to claim 1 which is a dicotyledonous plant.

27. The plant according to claim 26 which is a solanaceous plant.

28. The plant according to claim 27 which is a tomato plant.

29. The plant according to claim 27 which is a carrot plant.

30. The plant of claim 16 wherein said antifungal effect is with respect to the genus Alternaria.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGCTTGGATC CGTCGACGGT CCT    23

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATTAGGATC CGTCGACGGA TCCA    24

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATCCAACAT GAGGCTGTGC A    21

( 2 ) INFORMATION FOR SEQ ID NO:4:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:4:

AATTTGCACA GCCTCATGTT G    21

(2) INFORMATION FOR SEQ ID NO:5:

(i) SEQUENCE CHARACTERISTICS:
    (A) LENGTH: 11 base pairs
    (B) TYPE: nucleic acid
    (C) STRANDEDNESS: single
    (D) TOPOLOGY: linear (xi) SEQUENCE DESCRIPTION: SEQ ID NO:5:

GTCTCTGGTG G    11

(2) INFORMATION FOR SEQ ID NO:6:

(i) SEQUENCE CHARACTERISTICS:
    (A) LENGTH: 11 base pairs
    (B) TYPE: nucleic acid
    (C) STRANDEDNESS: single
    (D) TOPOLOGY: linear (xi) SEQUENCE DESCRIPTION: SEQ ID NO:6:

TGATATCGTT A    11

(2) INFORMATION FOR SEQ ID NO:7:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (xi) SEQUENCE DESCRIPTION: SEQ ID NO:7:

AATTGAGCTC    10

(2) INFORMATION FOR SEQ ID NO:8:

(i) SEQUENCE CHARACTERISTICS:
    (A) LENGTH: 966 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 25..786

(xi) SEQUENCE DESCRIPTION: SEQ ID NO:8:

```
GAATTCCTAA TAATCGCGAA AAAA ATG AAG TTC TGG GGA TCA GTA TTG GCA         51
                              Met Lys Phe Trp Gly Ser Val Leu Ala
                              1               5

TTG TCT TTT GTT GTG TTC TTG TTC CTA ACA GGA ACA CTG GCA CAA AAT         99
Leu Ser Phe Val Val Phe Leu Phe Leu Thr Gly Thr Leu Ala Gln Asn
10              15                  20                  25

GTT GGT TCT ATT GTG ACA AGC GAC TTA TTT GAC CAG ATG CTT AAA AAT        147
Val Gly Ser Ile Val Thr Ser Asp Leu Phe Asp Gln Met Leu Lys Asn
                30                  35                  40

AGG AAT GAT GCT AGA TGT TTT GCC GTA CGG TTT TAC ACT TAC GAT GCC        195
Arg Asn Asp Ala Arg Cys Phe Ala Val Arg Phe Tyr Thr Tyr Asp Ala
            45                  50                  55
```

| | | | | | | | | | | | | | | | | |
|---|---|---|---|---|---|---|---|---|---|---|---|---|---|---|---|---|
| TTC | ATA | GCT | GCT | GCC | AAT | TCG | TTC | CCA | GGT | TTT | GGA | ACT | ACT | GGT | GAT | 243 |
| Phe | Ile | Ala | Ala | Ala | Asn | Ser | Phe | Pro | Gly | Phe | Gly | Thr | Thr | Gly | Asp | |
| | | 60 | | | | | 65 | | | | | 70 | | | | |
| GAT | ACT | GCC | CGT | AAG | AAA | GAA | ATT | GCT | GCC | TTT | TTC | GGT | CAA | ACT | TCT | 291 |
| Asp | Thr | Ala | Arg | Lys | Lys | Glu | Ile | Ala | Ala | Phe | Phe | Gly | Gln | Thr | Ser | |
| | 75 | | | | | 80 | | | | | 85 | | | | | |
| CAT | GAA | ACT | ACT | GGT | GGT | ACC | TTA | AGT | CCA | GAT | GGT | CCA | TAT | GCA | GGA | 339 |
| His | Glu | Thr | Thr | Gly | Gly | Thr | Leu | Ser | Pro | Asp | Gly | Pro | Tyr | Ala | Gly | |
| 90 | | | | | 95 | | | | | 100 | | | | | 105 | |
| GGA | TAT | TGC | TTT | CTT | AGA | GAA | GGC | AAT | CAA | ATG | GGA | AAC | GGA | TAC | TAT | 387 |
| Gly | Tyr | Cys | Phe | Leu | Arg | Glu | Gly | Asn | Gln | Met | Gly | Asn | Gly | Tyr | Tyr | |
| | | | | 110 | | | | | 115 | | | | | 120 | | |
| GGC | AGA | GGA | CCC | ATC | CAA | TTG | ACA | GGC | CAA | TCT | AAC | TAT | GAC | TTA | GCT | 435 |
| Gly | Arg | Gly | Pro | Ile | Gln | Leu | Thr | Gly | Gln | Ser | Asn | Tyr | Asp | Leu | Ala | |
| | | | 125 | | | | | 130 | | | | | 135 | | | |
| GGG | AAA | GCT | ATT | GAA | CAA | GAC | TTA | GTT | AAC | AAC | CCT | GAT | TTA | GTA | GCA | 483 |
| Gly | Lys | Ala | Ile | Glu | Gln | Asp | Leu | Val | Asn | Asn | Pro | Asp | Leu | Val | Ala | |
| | | 140 | | | | | 145 | | | | | 150 | | | | |
| ACA | GAT | GCT | ACT | GTA | TCA | TTC | AAA | ACA | GCA | ATA | TGG | TTC | TGG | ATG | ACA | 531 |
| Thr | Asp | Ala | Thr | Val | Ser | Phe | Lys | Thr | Ala | Ile | Trp | Phe | Trp | Met | Thr | |
| | 155 | | | | | 160 | | | | | 165 | | | | | |
| CCA | CAG | GGT | AAC | AAG | CCA | TCT | TGC | CAC | GAC | GTT | ATC | ACC | GGC | CGA | TGG | 579 |
| Pro | Gln | Gly | Asn | Lys | Pro | Ser | Cys | His | Asp | Val | Ile | Thr | Gly | Arg | Trp | |
| 170 | | | | | 175 | | | | | 180 | | | | | 185 | |
| ACG | CCA | TCA | GCC | GCC | GAT | ACA | TCG | GCG | AAT | CGT | GTA | CCA | GGT | TAT | GGT | 627 |
| Thr | Pro | Ser | Ala | Ala | Asp | Thr | Ser | Ala | Asn | Arg | Val | Pro | Gly | Tyr | Gly | |
| | | | | 190 | | | | | 195 | | | | | 200 | | |
| GTC | ATT | ACT | AAC | ATA | ATT | AAT | GGT | GGA | ATT | GAA | TGT | GGC | AAA | GGT | CAG | 675 |
| Val | Ile | Thr | Asn | Ile | Ile | Asn | Gly | Gly | Ile | Glu | Cys | Gly | Lys | Gly | Gln | |
| | | | 205 | | | | | 210 | | | | | 215 | | | |
| AAT | GCA | CGA | GTG | GAA | GAT | CGA | ATT | GGA | TAT | TAC | AGG | AGG | AAT | GTA | AGT | 723 |
| Asn | Ala | Arg | Val | Glu | Asp | Arg | Ile | Gly | Tyr | Tyr | Arg | Arg | Asn | Val | Ser | |
| | | 220 | | | | | 225 | | | | | 230 | | | | |
| ATA | ATG | AAC | GTG | GCC | CCT | GGA | GAC | AAT | TTG | GAT | TGT | TAC | AAC | CAA | AGG | 771 |
| Ile | Met | Asn | Val | Ala | Pro | Gly | Asp | Asn | Leu | Asp | Cys | Tyr | Asn | Gln | Arg | |
| | 235 | | | | | 240 | | | | | 245 | | | | | |
| AAC | TTT | GCC | GAA | GTC | TAGGCTGGTC | ACATTATGAG | TGCAAATGTT | ATGTAGTCAT | | | | | | | | 826 |
| Asn | Phe | Ala | Glu | Val | | | | | | | | | | | | |
| 250 | | | | | | | | | | | | | | | | |

GGAGATGACA GTATACAACT TATATTTGAA TGTAATAAAT AAGGGATTCT CTATGCCCAT 886

TTATGATAGA GTGAAATATA TTATTGTTTG TCTTCTTGGA AGAAGTAGA ACCAACAGTT 946

CCTTTAAAAA AAAGGAATTC 966

( 2 ) INFORMATION FOR SEQ ID NO:9:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| | | | | | | | | | | | | | | |
|---|---|---|---|---|---|---|---|---|---|---|---|---|---|---|
| Met | Lys | Phe | Trp | Gly | Ser | Val | Leu | Ala | Leu | Ser | Phe | Val | Val | Phe | Leu |
| 1 | | | | 5 | | | | | 10 | | | | | 15 | |
| Phe | Leu | Thr | Gly | Thr | Leu | Ala | Gln | Asn | Val | Gly | Ser | Ile | Val | Thr | Ser |
| | | | 20 | | | | | 25 | | | | | 30 | | |
| Asp | Leu | Phe | Asp | Gln | Met | Leu | Lys | Asn | Arg | Asn | Asp | Ala | Arg | Cys | Phe |
| | | 35 | | | | | 40 | | | | | 45 | | | |

```
Ala  Val  Arg  Phe  Tyr  Thr  Tyr  Asp  Ala  Phe  Ile  Ala  Ala  Ala  Asn  Ser
     50                  55                           60

Phe  Pro  Gly  Phe  Gly  Thr  Thr  Gly  Asp  Asp  Thr  Ala  Arg  Lys  Lys  Glu
65                       70                  75                           80

Ile  Ala  Ala  Phe  Phe  Gly  Gln  Thr  Ser  His  Glu  Thr  Thr  Gly  Gly  Thr
                    85                  90                           95

Leu  Ser  Pro  Asp  Gly  Pro  Tyr  Ala  Gly  Gly  Tyr  Cys  Phe  Leu  Arg  Glu
               100                 105                      110

Gly  Asn  Gln  Met  Gly  Asn  Gly  Tyr  Tyr  Gly  Arg  Gly  Pro  Ile  Gln  Leu
               115                 120                      125

Thr  Gly  Gln  Ser  Asn  Tyr  Asp  Leu  Ala  Gly  Lys  Ala  Ile  Glu  Gln  Asp
     130                 135                 140

Leu  Val  Asn  Asn  Pro  Asp  Leu  Val  Ala  Thr  Asp  Ala  Thr  Val  Ser  Phe
145                      150                 155                           160

Lys  Thr  Ala  Ile  Trp  Phe  Trp  Met  Thr  Pro  Gln  Gly  Asn  Lys  Pro  Ser
                    165                 170                      175

Cys  His  Asp  Val  Ile  Thr  Gly  Arg  Trp  Thr  Pro  Ser  Ala  Ala  Asp  Thr
               180                 185                      190

Ser  Ala  Asn  Arg  Val  Pro  Gly  Tyr  Gly  Val  Ile  Thr  Asn  Ile  Ile  Asn
     195                 200                 205

Gly  Gly  Ile  Glu  Cys  Gly  Lys  Gly  Gln  Asn  Ala  Arg  Val  Glu  Asp  Arg
     210                 215                 220

Ile  Gly  Tyr  Tyr  Arg  Arg  Asn  Val  Ser  Ile  Met  Asn  Val  Ala  Pro  Gly
225                      230                 235                           240

Asp  Asn  Leu  Asp  Cys  Tyr  Asn  Gln  Arg  Asn  Phe  Ala  Glu  Val
                    245                 250
```

(2) INFORMATION FOR SEQ ID NO:10:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 10..981

(xi) SEQUENCE DESCRIPTION: SEQ ID NO:10:

```
GGATCCAAC ATG AGG CTG TGC AAA TTC ACA GCT CTT TCT TCT CTA CTC            48
          Met Arg Leu Cys Lys Phe Thr Ala Leu Ser Ser Leu Leu
           1               5                   10

TTT TCT CTC CTA CTC CTC TCT GCC TCG GCA GAA CAA TGT GGT TCG CAG          96
Phe Ser Leu Leu Leu Leu Ser Ala Ser Ala Glu Gln Cys Gly Ser Gln
        15                  20                  25

GCG GGA GGT GCG CGT TGT GCC TCG GGT CTC TGC TGC AGC AAA TTT GGT         144
Ala Gly Gly Ala Arg Cys Ala Ser Gly Leu Cys Cys Ser Lys Phe Gly
30                  35                  40                  45

TGG TGT GGT AAC ACC AAT GAC TAT TGT GGC CCT GGC AAT TGC CAG AGC         192
Trp Cys Gly Asn Thr Asn Asp Tyr Cys Gly Pro Gly Asn Cys Gln Ser
                50                  55                  60

CAG TGC CCT GGT GGT CCC ACA CCA CCC GGT GGT GGG GAT CTC GGC AGT         240
Gln Cys Pro Gly Gly Pro Thr Pro Pro Gly Gly Gly Asp Leu Gly Ser
            65                  70                  75

ATC ATC TCA AGT TCC ATG TTT GAT CAG ATG CTT AAG CAT CGC AAC GAT         288
Ile Ile Ser Ser Ser Met Phe Asp Gln Met Leu Lys His Arg Asn Asp
            80                  85                  90

AAT GCA TGC CAA GGA AAG GGA TTC TAC AGT TAC AAT GCC TTT ATC AAT         336
Asn Ala Cys Gln Gly Lys Gly Phe Tyr Ser Tyr Asn Ala Phe Ile Asn
```

-continued

```
          95                              100                             105
GCT  GCT  AGG  TCT  TTT  CCT  GGC  TTT  GGT  ACT  AGT  GGT  GAT  ACC  ACT  GCC        384
Ala  Ala  Arg  Ser  Phe  Pro  Gly  Phe  Gly  Thr  Ser  Gly  Asp  Thr  Thr  Ala
110                      115                      120                      125

CGT  AAA  AGA  GAA  ATC  GCG  GCT  TTC  TTC  GCC  CAA  ACC  TCC  CAT  GAA  ACT        432
Arg  Lys  Arg  Glu  Ile  Ala  Ala  Phe  Phe  Ala  Gln  Thr  Ser  His  Glu  Thr
                         130                      135                      140

ACA  GGA  GGA  TGG  GCA  ACA  GCA  CCA  GAT  GGT  CCA  TAC  GCG  TGG  GGT  TAC        480
Thr  Gly  Gly  Trp  Ala  Thr  Ala  Pro  Asp  Gly  Pro  Tyr  Ala  Trp  Gly  Tyr
               145                      150                      155

TGC  TGG  CTT  AGA  GAA  CAA  TGT  AGC  CCC  GGC  GAC  TAC  TGT  ACA  CCA  AGT        528
Cys  Trp  Leu  Arg  Glu  Gln  Cys  Ser  Pro  Gly  Asp  Tyr  Cys  Thr  Pro  Ser
          160                      165                      170

GGT  CAG  TGG  CCT  TGT  GCT  CCT  GGT  CGG  AAA  TAT  TTC  GGA  CGA  GGC  CCC        576
Gly  Gln  Trp  Pro  Cys  Ala  Pro  Gly  Arg  Lys  Tyr  Phe  Gly  Arg  Gly  Pro
175                      180                      185

ATC  CAA  ATT  TCA  CAC  AAC  TAC  AAC  TAC  GGA  CCT  TGT  GGA  AGA  GCC  ATA        624
Ile  Gln  Ile  Ser  His  Asn  Tyr  Asn  Tyr  Gly  Pro  Cys  Gly  Arg  Ala  Ile
190                      195                      200                      205

GGA  GTG  GAC  CTC  CTA  AAC  AAT  CCT  GAT  TTA  GTG  GCC  ACA  GAT  CCA  GTA        672
Gly  Val  Asp  Leu  Leu  Asn  Asn  Pro  Asp  Leu  Val  Ala  Thr  Asp  Pro  Val
                    210                      215                      220

ATC  TCA  TTC  AAG  TCA  GCT  CTC  TGG  TTT  TGG  ATG  ACT  CCT  CAA  TCA  CCA        720
Ile  Ser  Phe  Lys  Ser  Ala  Leu  Trp  Phe  Trp  Met  Thr  Pro  Gln  Ser  Pro
               225                      230                      235

AAA  CCT  TCT  TGC  CAC  GAT  GTC  ATC  ATT  GGA  AGA  TGG  CAA  CCA  TCG  TCT        768
Lys  Pro  Ser  Cys  His  Asp  Val  Ile  Ile  Gly  Arg  Trp  Gln  Pro  Ser  Ser
          240                      245                      250

GCT  GAC  CGC  GCA  GCC  AAT  CGT  CTC  CCT  GGA  TTT  GGT  GTC  ATC  ACG  AAC        816
Ala  Asp  Arg  Ala  Ala  Asn  Arg  Leu  Pro  Gly  Phe  Gly  Val  Ile  Thr  Asn
255                      260                      265

ATC  ATC  AAT  GGT  GGC  TTG  GAA  TGT  GGT  CGT  GGC  ACT  GAC  TCA  AGG  GTC        864
Ile  Ile  Asn  Gly  Gly  Leu  Glu  Cys  Gly  Arg  Gly  Thr  Asp  Ser  Arg  Val
270                      275                      280                      285

CAG  GAT  CGC  ATT  GGG  TTT  TAC  AGG  AGG  TAT  TGC  AGT  ATT  CTT  GGT  GTT        912
Gln  Asp  Arg  Ile  Gly  Phe  Tyr  Arg  Arg  Tyr  Cys  Ser  Ile  Leu  Gly  Val
                    290                      295                      300

AGT  CCT  GGT  GAC  AAT  CTT  GAT  TGC  GGA  AAC  CAG  AGG  TCT  TTT  GGA  AAC        960
Ser  Pro  Gly  Asp  Asn  Leu  Asp  Cys  Gly  Asn  Gln  Arg  Ser  Phe  Gly  Asn
               305                      310                      315

GGA  CTT  TTA  GTC  GAT  ACT  ATG  TAATTTATG  GTCTGTTTG  TTGAATCCCT                  1011
Gly  Leu  Leu  Val  Asp  Thr  Met
          320

TTGCGACGCA  GGGACCAGGG  GCTATGAATA  AAGTTAATGT  GTGAATTGTG  TGATTGTCAT            1071

CTATGGGATC  GCGACTATAA  TCGTTTATAA  TAAACAAAGA  CTTGTCCACA  AAAAAAAAAA            1131

GGAATTAATT  CCCGGGGATC  C                                                         1152
```

( 2 ) INFORMATION FOR SEQ ID NO:11:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Arg  Leu  Cys  Lys  Phe  Thr  Ala  Leu  Ser  Ser  Leu  Leu  Phe  Ser  Leu
 1              5                        10                       15

Leu  Leu  Leu  Ser  Ala  Ser  Ala  Glu  Gln  Cys  Gly  Ser  Gln  Ala  Gly  Gly
```

|  |  |  | 20 |  |  |  | 25 |  |  |  |  | 30 |  |  |
|---|---|---|---|---|---|---|---|---|---|---|---|---|---|---|

Ala Arg Cys Ala Ser Gly Leu Cys Cys Ser Lys Phe Gly Trp Cys Gly
            35                      40                      45

Asn Thr Asn Asp Tyr Cys Gly Pro Gly Asn Cys Gln Ser Gln Cys Pro
        50                      55                      60

Gly Gly Pro Thr Pro Pro Gly Gly Gly Asp Leu Gly Ser Ile Ile Ser
65                          70                      75                      80

Ser Ser Met Phe Asp Gln Met Leu Lys His Arg Asn Asp Asn Ala Cys
                        85                      90                      95

Gln Gly Lys Gly Phe Tyr Ser Tyr Asn Ala Phe Ile Asn Ala Ala Arg
                100                     105                     110

Ser Phe Pro Gly Phe Gly Thr Ser Gly Asp Thr Thr Ala Arg Lys Arg
        115                     120                     125

Glu Ile Ala Ala Phe Phe Ala Gln Thr Ser His Glu Thr Thr Gly Gly
130                     135                     140

Trp Ala Thr Ala Pro Asp Gly Pro Tyr Ala Trp Gly Tyr Cys Trp Leu
145                     150                     155                     160

Arg Glu Gln Cys Ser Pro Gly Asp Tyr Cys Thr Pro Ser Gly Gln Trp
                165                     170                     175

Pro Cys Ala Pro Gly Arg Lys Tyr Phe Gly Arg Gly Pro Ile Gln Ile
            180                     185                     190

Ser His Asn Tyr Asn Tyr Gly Pro Cys Gly Arg Ala Ile Gly Val Asp
        195                     200                     205

Leu Leu Asn Asn Pro Asp Leu Val Ala Thr Asp Pro Val Ile Ser Phe
210                     215                     220

Lys Ser Ala Leu Trp Phe Trp Met Thr Pro Gln Ser Pro Lys Pro Ser
225                     230                     235                     240

Cys His Asp Val Ile Ile Gly Arg Trp Gln Pro Ser Ser Ala Asp Arg
                245                     250                     255

Ala Ala Asn Arg Leu Pro Gly Phe Gly Val Ile Thr Asn Ile Ile Asn
            260                     265                     270

Gly Gly Leu Glu Cys Gly Arg Gly Thr Asp Ser Arg Val Gln Asp Arg
        275                     280                     285

Ile Gly Phe Tyr Arg Arg Tyr Cys Ser Ile Leu Gly Val Ser Pro Gly
290                     295                     300

Asp Asn Leu Asp Cys Gly Asn Gln Arg Ser Phe Gly Asn Gly Leu Leu
305                     310                     315                     320

Val Asp Thr Met ( 2 ) INFORMATION FOR SEQ ID NO:12:

( i ) SEQUENCE CHARACTERISTICS:
        ( A ) LENGTH: 2020 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(94..175, 517..1463)

( x i ) SEQUENCE DESCRIPTION: SEQ ID NO:12:

```
CTTCTGCTTG TCTATATAAG AAGCAGCCTA ATGGTTCCTT AAACACACAA TTTCAGCTCA        60

AGTGTTTCTT ACTCTCTCAT TTCCATTTTA GCT ATG ACT TTA TGC ATT AAA AAT       114
                                    Met Thr Leu Cys Ile Lys Asn
                                     1               5

GGC TTT CTT GCA GCT GCC CTT GTA CTT GTT GGG CTG TTA ATT TGC AGT        162
```

```
Gly Phe Leu Ala Ala Ala Leu Val Leu Val Gly Leu Leu Ile Cys Ser
         10                  15                  20

ATC CAA ATG ATA   G GTCTCTCTCT CTCACACACA CACACTTTCT CTCATGATAC          215
Ile Gln Met Ile
         25

ATGTACATGC ACCTTGTATG ATGCGGATCA ACTTATGTAC ACTAATAGCG TAAATAATTT        275

TTACAATATA TATTAGGATT AATATATTTT AACATGTTGT GTCAGGTAAT CTACCTTATT       335

TATTAAGTCA CTTATTATGA ATAGTTACTT ATAGTTACTT CTGGGTGACC CGACACTATA       395

ATGTTGGCTA GAGAAGAACT TAAATAGAGA ATCATGGTTA GTGAGAATAT TCATTTATTC       455

GACACCAACT TATTTGGGGA CTGAAACTTC TTTGTAATAT ACTCTTTTC TTACAATCCA        515

G  GG GCA CAA TCT ATT GGA GTA TGC TAT GGA AAA CAT GCA AAC AAT           560
     Gly Ala Gln Ser Ile Gly Val Cys Tyr Gly Lys His Ala Asn Asn
              30                  35                  40

TTA CCA TCA GAC CAA GAT GTT ATA AAC CTA TAC AAT GCT AAT GGC ATC         608
Leu Pro Ser Asp Gln Asp Val Ile Asn Leu Tyr Asn Ala Asn Gly Ile
             45                  50                  55

AGA AAG ATG AGA ATC TAC AAT CCA GAT ACA AAT GTC TTC AAC GCT CTC         656
Arg Lys Met Arg Ile Tyr Asn Pro Asp Thr Asn Val Phe Asn Ala Leu
         60                  65                  70

AGA GGA AGT AAC ATT GAG ATC ATT CTC GAC GTC CCA CTT CAA GAT CTT         704
Arg Gly Ser Asn Ile Glu Ile Ile Leu Asp Val Pro Leu Gln Asp Leu
 75                  80                  85                  90

CAA TCC CTA ACT GAT CCT TCA AGA GCC AAT GGA TGG GTC CAA GAT AAC         752
Gln Ser Leu Thr Asp Pro Ser Arg Ala Asn Gly Trp Val Gln Asp Asn
             95                 100                 105

ATA ATA AAT CAT TTC CCA GAT GTT AAA TTT AAA TAT ATA GCT GTT GGA         800
Ile Ile Asn His Phe Pro Asp Val Lys Phe Lys Tyr Ile Ala Val Gly
             110                 115                 120

AAT GAA GTC TCT CCC GGA AAT AAT GGT CAA TAT GCA CCA TTT GTT GCT         848
Asn Glu Val Ser Pro Gly Asn Asn Gly Gln Tyr Ala Pro Phe Val Ala
         125                 130                 135

CCT GCC ATG CAA AAT GTA TAT AAT GCA TTA GCA GCA GCA GGG TTG CAA         896
Pro Ala Met Gln Asn Val Tyr Asn Ala Leu Ala Ala Ala Gly Leu Gln
         140                 145                 150

GAT CAA ATC AAG GTC TCA ACT GCA ACA TAT TCA GGG ATC TTA GCG AAT         944
Asp Gln Ile Lys Val Ser Thr Ala Thr Tyr Ser Gly Ile Leu Ala Asn
155                 160                 165                 170

ACC TAC CCG CCC AAA GAT AGT ATT TTT CGA GGA GAA TTC AAT AGT TTC         992
Thr Tyr Pro Pro Lys Asp Ser Ile Phe Arg Gly Glu Phe Asn Ser Phe
                 175                 180                 185

ATT AAT CCC ATA ATC CAA TTT CTA GTA CAA CAT AAC CTT CCA CTC TTA         1040
Ile Asn Pro Ile Ile Gln Phe Leu Val Gln His Asn Leu Pro Leu Leu
             190                 195                 200

GCC AAT GTC TAT CCT TAT TTT GGT CAC ATT TTC AAC ACT GCT GAT GTC         1088
Ala Asn Val Tyr Pro Tyr Phe Gly His Ile Phe Asn Thr Ala Asp Val
         205                 210                 215

CCA CTT TCT TAT GCT TTG TTC ACA CAA CAA GAA GCA AAT CCT GCA GGA         1136
Pro Leu Ser Tyr Ala Leu Phe Thr Gln Gln Glu Ala Asn Pro Ala Gly
         220                 225                 230

TAT CAA AAT CTT TTT GAT GCC CTT TTG GAT TCT ATG TAT TTT GCT GTA         1184
Tyr Gln Asn Leu Phe Asp Ala Leu Leu Asp Ser Met Tyr Phe Ala Val
235                 240                 245                 250

GAG AAA GCT GGA GGA CAA AAT GTG GAG ATT ATT GTA TCT GAA AGT GGC         1232
Glu Lys Ala Gly Gly Gln Asn Val Glu Ile Ile Val Ser Glu Ser Gly
             255                 260                 265

TGG CCT TCT GAA GGA AAC TCT GCA GCA ACT ATT GAA AAT GCT CAA ACT         1280
Trp Pro Ser Glu Gly Asn Ser Ala Ala Thr Ile Glu Asn Ala Gln Thr
         270                 275                 280
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| TAC | TAT | GAA | AAT | TTG | ATT | AAT | CAT | GTG | AAA | AGC | GGG | GCA | GGA | ACT | CCA | 1328 |
| Tyr | Tyr | Glu | Asn | Leu | Ile | Asn | His | Val | Lys | Ser | Gly | Ala | Gly | Thr | Pro |      |
|     |     | 285 |     |     |     |     | 290 |     |     |     |     | 295 |     |     |     |      |
| AAG | AAA | CCT | GGA | AAG | GCT | ATA | GAA | ACT | TAT | TTA | TTT | GCC | ATG | TTT | GAT | 1376 |
| Lys | Lys | Pro | Gly | Lys | Ala | Ile | Glu | Thr | Tyr | Leu | Phe | Ala | Met | Phe | Asp |      |
|     | 300 |     |     |     |     | 305 |     |     |     |     | 310 |     |     |     |     |      |
| GAA | AAT | AAT | AAG | GAA | GGA | GAT | ATC | ACA | GAG | AAA | CAC | TTT | GGA | CTC | TTT | 1424 |
| Glu | Asn | Asn | Lys | Glu | Gly | Asp | Ile | Thr | Glu | Lys | His | Phe | Gly | Leu | Phe |      |
| 315 |     |     |     |     | 320 |     |     |     |     | 325 |     |     |     |     | 330 |      |
| TCT | CCT | GAT | CAG | AGG | GCA | AAA | TAT | CAA | CTC | AAT | TTC | AAT | TAATTAATGC |   |   | 1473 |
| Ser | Pro | Asp | Gln | Arg | Ala | Lys | Tyr | Gln | Leu | Asn | Phe | Asn |     |     |     |      |
|     |     |     | 335 |     |     |     |     |     | 340 |     |     |     |     |     |     |      |

| | | |
|---|---|---|
| ATGGTAACAT | TTATTGATAT ATATAGTGAT ATGAGTAATA AGGAGAAGTA GAACTGCTAT | 1533 |
| GTTTTCTCT | TCAATTGAAA ATGTAACTCT GGTTTCACTT TGATATTTAT ATGACATATT | 1593 |
| TATTGAGATC | TCGTCTTTTG TTTTAAATTC TTGCCTTCTA TTGGCAAATA TCTGCGTAAT | 1653 |
| TTTCATTTGT | TTTAAAAATT ACTAAGCCTC AAAAGAGTGA CTACCAATAT ATTCTTGATT | 1713 |
| ATTAATATTC | CCCGTGCTTG GGGGACCGGG TGAGGTGGGG GGTGGGGGGG ATGACGAAAA | 1773 |
| AAGTTAATGA | AAAACCGGTT TGCATTGGAT GCTCTTTTA ACCTCCCCAA AATATGATGG | 1833 |
| TTTTGTTGTC | TTGGAGAGTG TTTAAGCTAC TTCTTCTCAA GAATTTTCTT GGTCAGTTCT | 1893 |
| TAACGTAATT | GCTTTTAATT TCTTAATTAT CGGTAACCCT TCGAAACAAA AGGAAAATTA | 1953 |
| AGCTAGGAGA | TGACTCGTAT TCATAATGTT TTACCTTGGA TCAACCCCGC CTTTATATTT | 2013 |
| CATACGA | | 2020 |

( 2 ) INFORMATION FOR SEQ ID NO:13:

( i ) SEQUENCE CHARACTERISTICS:
( A ) LENGTH: 343 amino acids
( B ) TYPE: amino acid
( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Met | Thr | Leu | Cys | Ile | Lys | Asn | Gly | Phe | Leu | Ala | Ala | Ala | Leu | Val | Leu |
| 1 | | | | 5 | | | | | 10 | | | | | 15 | |
| Val | Gly | Leu | Leu | Ile | Cys | Ser | Ile | Gln | Met | Ile | Gly | Ala | Gln | Ser | Ile |
| | | | 20 | | | | | 25 | | | | | 30 | | |
| Gly | Val | Cys | Tyr | Gly | Lys | His | Ala | Asn | Asn | Leu | Pro | Ser | Asp | Gln | Asp |
| | | 35 | | | | | 40 | | | | | 45 | | | |
| Val | Ile | Asn | Leu | Tyr | Asn | Ala | Asn | Gly | Ile | Arg | Lys | Met | Arg | Ile | Tyr |
| | 50 | | | | | 55 | | | | | 60 | | | | |
| Asn | Pro | Asp | Thr | Asn | Val | Phe | Asn | Ala | Leu | Arg | Gly | Ser | Asn | Ile | Glu |
| 65 | | | | | 70 | | | | | 75 | | | | | 80 |
| Ile | Ile | Leu | Asp | Val | Pro | Leu | Gln | Asp | Leu | Gln | Ser | Leu | Thr | Asp | Pro |
| | | | | 85 | | | | | 90 | | | | | 95 | |
| Ser | Arg | Ala | Asn | Gly | Trp | Val | Gln | Asp | Asn | Ile | Ile | Asn | His | Phe | Pro |
| | | | | 100 | | | | | 105 | | | | | 110 | |
| Asp | Val | Lys | Phe | Lys | Tyr | Ile | Ala | Val | Gly | Asn | Glu | Val | Ser | Pro | Gly |
| | | | 115 | | | | | 120 | | | | | 125 | | |
| Asn | Asn | Gly | Gln | Tyr | Ala | Pro | Phe | Val | Ala | Pro | Ala | Met | Gln | Asn | Val |
| | | 130 | | | | | 135 | | | | | 140 | | | |
| Tyr | Asn | Ala | Leu | Ala | Ala | Ala | Gly | Leu | Gln | Asp | Gln | Ile | Lys | Val | Ser |
| 145 | | | | | 150 | | | | | 155 | | | | | 160 |
| Thr | Ala | Thr | Tyr | Ser | Gly | Ile | Leu | Ala | Asn | Thr | Tyr | Pro | Pro | Lys | Asp |

|  |  | 165 |  |  |  |  |  | 170 |  |  |  |  | 175 |  |
|---|---|---|---|---|---|---|---|---|---|---|---|---|---|---|
| Ser | Ile | Phe | Arg | Gly | Glu | Phe | Asn | Ser | Phe | Ile | Asn | Pro | Ile | Ile | Gln |
|  |  |  | 180 |  |  |  |  | 185 |  |  |  | 190 |  |  |  |

```
Phe Leu Val Gln His Asn Leu Pro Leu Leu Ala Asn Val Tyr Pro Tyr
            195                 200                 205

Phe Gly His Ile Phe Asn Thr Ala Asp Val Pro Leu Ser Tyr Ala Leu
            210             215                 220

Phe Thr Gln Gln Glu Ala Asn Pro Ala Gly Tyr Gln Asn Leu Phe Asp
225                 230                 235                 240

Ala Leu Leu Asp Ser Met Tyr Phe Ala Val Glu Lys Ala Gly Gly Gln
                245                 250                 255

Asn Val Glu Ile Ile Val Ser Glu Ser Gly Trp Pro Ser Glu Gly Asn
            260                 265                 270

Ser Ala Ala Thr Ile Glu Asn Ala Gln Thr Tyr Tyr Glu Asn Leu Ile
            275                 280                 285

Asn His Val Lys Ser Gly Ala Gly Thr Pro Lys Lys Pro Gly Lys Ala
            290                 295                 300

Ile Glu Thr Tyr Leu Phe Ala Met Phe Asp Glu Asn Asn Lys Glu Gly
305                 310                 315                 320

Asp Ile Thr Glu Lys His Phe Gly Leu Phe Ser Pro Asp Gln Arg Ala
                325                 330                 335

Lys Tyr Gln Leu Asn Phe Asn
                340
```

( 2 ) INFORMATION FOR SEQ ID NO:14:

( i ) SEQUENCE CHARACTERISTICS:
        ( A ) LENGTH: 2509 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(85..142, 930..1948)

( x i ) SEQUENCE DESCRIPTION: SEQ ID NO:14:

```
AATATAAATA GCTCGTTGTT CATCTTAATT CTCCCAACAA GTCTTCCCAT CATGTCTACC         60

TCACATAAAC ATAATACTCC TCAA ATG GCT GCT ATC ACA CTC CTA GGA TTA          111
                          Met Ala Ala Ile Thr Leu Leu Gly Leu
                           1               5

CTA CTT GTT GCC AGC AGC ATT GAC ATA GCA  G GTTCTGGTC AAATATTTGA         162
Leu Leu Val Ala Ser Ser Ile Asp Ile Ala
 10              15

ACTTCCCAGC CAAAAATATT GTCTTATAAT TTGTGTGCG CAAAATTTTA ATTTAGTTGA         222

TAGTTATTTG CTTATTTTTC TTTTCAAATT GCTTGTGTTT TTTTCTCAAA TTAACTTGCA         282

CCGTATTCAT TTAGCGATAG TTATTTGCTC TATTTGTGT AACACTCACT CACAAACTTT         342

TCAATTTGAG GGGAGGACAG TGAATCTAAG ATTGAAATTT ATGAGTTTAA TTAGACTAAT         402

TCCCATTTGA TTTATTGGCT AGAAGTCAAT TATTTGCATA GTGAGTCTTT TAACACACAG         462

ATTTGAGTTA AAGCTACTAC GTTCGTATTA ACCCATAACA TATACACCTT CTGTTCTAAT         522

TTCTTTGACA CTTTTTGTTA GTTTGTTCCA AAAAGGACGG ACATATTTGA TATTTGAGAA         582

TACTTTACCT TAACCTTAAT AGAATTTTTT ATGACATCAC ATATATTATG GAATATATAC         642

GACCATAATT TTCAAATATC TTATAGTCGT ACAAATATTA TAGCATGTTT AATACCACAA         702

CTTTCAAATT CTTCTTTTCC TTAAAAACAA AATATGTCAC ATAAATTAAA ATAGAGGAAG         762
```

-continued

| | |
|---|---|
| TATACTACAT CAATCAGCCC CTAGTGGAGG GGACCTACTG TAAGTTTTTA AGTTTTCAAG | 822 |
| AATTCAGTAA TTGATTAGGA GCCCGTCTGG ACATAAAAAA AAATTCCTTT TTTTCCAAAA | 882 |
| AATGCCCACT AAATTCTAAC ACTATTTTG TAATTCTTAT TGAGCAG   GG GCT CAA<br>                                                                           Gly Ala Gln<br>                                                                          20 | 937 |
| TCG ATA GGT GTT TGC TAT GGA ATG CTA GGC AAC AAC TTG CCA AAT CAT<br>Ser Ile Gly Val Cys Tyr Gly Met Leu Gly Asn Asn Leu Pro Asn His<br>         25                             30                           35 | 985 |
| TGG GAA GTT ATA CAG CTC TAC AAG TCA AGA AAC ATA GGA AGA CTG AGG<br>Trp Glu Val Ile Gln Leu Tyr Lys Ser Arg Asn Ile Gly Arg Leu Arg<br>    40                         45                              50 | 1033 |
| CTT TAT GAT CCA AAT CAT GGA GCT TTA CAA GCA TTA AAA GGC TCA AAT<br>Leu Tyr Asp Pro Asn His Gly Ala Leu Gln Ala Leu Lys Gly Ser Asn<br>55                       60                        65                       70 | 1081 |
| ATT GAA GTT ATG TTA GGA CTT CCC AAT TCA GAT GTG AAG CAC ATT GCT<br>Ile Glu Val Met Leu Gly Leu Pro Asn Ser Asp Val Lys His Ile Ala<br>                   75                             80                           85 | 1129 |
| TCC GGA ATG GAA CAT GCA AGA TGG TGG GTA CAG AAA AAT GTT AAA GAT<br>Ser Gly Met Glu His Ala Arg Trp Trp Val Gln Lys Asn Val Lys Asp<br>            90                             95                          100 | 1177 |
| TTC TGG CCA GAT GTT AAG ATT AAG TAT ATT GCT GTT GGG AAT GAA ATC<br>Phe Trp Pro Asp Val Lys Ile Lys Tyr Ile Ala Val Gly Asn Glu Ile<br>       105                          110                         115 | 1225 |
| AGC CCT GTC ACT GGC ACA TCT TAC CTA ACC TCA TTT CTT ACT CCT GCT<br>Ser Pro Val Thr Gly Thr Ser Tyr Leu Thr Ser Phe Leu Thr Pro Ala<br>    120                         125                         130 | 1273 |
| ATG GTA AAT ATT TAC AAA GCA ATT GGT GAA GCT GGT TTG GGA AAC AAC<br>Met Val Asn Ile Tyr Lys Ala Ile Gly Glu Ala Gly Leu Gly Asn Asn<br>135                     140                        145                       150 | 1321 |
| ATC AAG GTC TCA ACT TCT GTA GAC ATG ACC TTG ATT GGA AAC TCT TAT<br>Ile Lys Val Ser Thr Ser Val Asp Met Thr Leu Ile Gly Asn Ser Tyr<br>                   155                          160                       165 | 1369 |
| CCA CCA TCA CAG GGT TCG TTT AGG AAC GAT GCT AGG TGG TTT GTT GAT<br>Pro Pro Ser Gln Gly Ser Phe Arg Asn Asp Ala Arg Trp Phe Val Asp<br>            170                         175                         180 | 1417 |
| GCC ATT GTT GGC TTC TTA AGG GAC ACA CGT GCA CCT TTA CTC GTT AAC<br>Ala Ile Val Gly Phe Leu Arg Asp Thr Arg Ala Pro Leu Leu Val Asn<br>         185                          190                         195 | 1465 |
| ATT TAC CCC TAT TTC AGT TAT TCT GGT AAT CCA GGC CAG ATT TCT CTC<br>Ile Tyr Pro Tyr Phe Ser Tyr Ser Gly Asn Pro Gly Gln Ile Ser Leu<br>    200                         205                         210 | 1513 |
| CCC TAT TCT CTT TTT ACA GCA CCA AAT GTG GTG GTA CAA GAT GGT TCC<br>Pro Tyr Ser Leu Phe Thr Ala Pro Asn Val Val Val Gln Asp Gly Ser<br>215                     220                        225                       230 | 1561 |
| CGC CAA TAT AGG AAC TTA TTT GAT GCA ATG CTG GAT TCT GTG TAT GCT<br>Arg Gln Tyr Arg Asn Leu Phe Asp Ala Met Leu Asp Ser Val Tyr Ala<br>                   235                          240                       245 | 1609 |
| GCC CTC GAG CGA TCA GGA GGG GCA TCT GTA GGG ATT GTT GTG TCC GAG<br>Ala Leu Glu Arg Ser Gly Gly Ala Ser Val Gly Ile Val Val Ser Glu<br>            250                       255                         260 | 1657 |
| AGT GGC TGG CCA TCT GCT GGT GCA TTT GGA GCC ACA TAT GAC AAT GCA<br>Ser Gly Trp Pro Ser Ala Gly Ala Phe Gly Ala Thr Tyr Asp Asn Ala<br>         265                          270                         275 | 1705 |
| GCA ACT TAC TTG AGG AAC TTA ATT CAA CAC GCT AAA GAG GGT AGC CCA<br>Ala Thr Tyr Leu Arg Asn Leu Ile Gln His Ala Lys Glu Gly Ser Pro<br>    280                         285                         290 | 1753 |
| AGA AAG CCT GGA CCT ATT GAG ACC TAT ATA TTT GCC ATG TTT GAT GAG<br>Arg Lys Pro Gly Pro Ile Glu Thr Tyr Ile Phe Ala Met Phe Asp Glu<br>295                     300                        305                       310 | 1801 |

| AAC | AAC | AAG | AAC | CCT | GAA | CTG | GAG | AAA | CAT | TTT | GGA | TTG | TTT | TCC | CCC | 1849 |
| Asn | Asn | Lys | Asn | Pro | Glu | Leu | Glu | Lys | His | Phe | Gly | Leu | Phe | Ser | Pro | |
| | | | | 315 | | | | 320 | | | | | | 325 | | |
| AAC | AAG | CAG | CCC | AAA | TAT | AAT | ATC | AAC | TTT | GGG | GTC | TCT | GGT | GGA | GTT | 1897 |
| Asn | Lys | Gln | Pro | Lys | Tyr | Asn | Ile | Asn | Phe | Gly | Val | Ser | Gly | Gly | Val | |
| | | | 330 | | | | | 335 | | | | | 340 | | | |
| TGG | GAC | AGT | TCA | GTT | GAA | ACT | AAT | GCT | ACT | GCT | TCT | CTC | GTA | AGT | GAG | 1945 |
| Trp | Asp | Ser | Ser | Val | Glu | Thr | Asn | Ala | Thr | Ala | Ser | Leu | Val | Ser | Glu | |
| | | | 345 | | | | 350 | | | | | 355 | | | | |

```
ATG TGAGCTGATG AGACACTTGA AATCTCTTTA CATACGTATT CCTTGGATGG       1998
Met

AAAACCTAGT AAAAACAAGA GAAATTTTTT CTTTATGCAA GATACTAAAT AACATTGCAT  2058
GTCTCTGTAA GTCCTCATGG ATTGTTATCC AGTGACGATG CAACTCTGAG TGGTTTTAAA  2118
TTCCTTTTCT TTGTGATATT GGTAATTTGG CAAGAAACTT TCTGTAAGTT TGTGAATTTC  2178
ATGCATCATT AATTATACAT CAGTTCCATG TTTGATCAGA TTGGGATTTG GTAACTTCAA  2238
TGTTAGTATT ATAATTAGTG TCTTTATCAT TGACTATCAA TTAATCTTTA TTTGGCAAGG  2298
CTTGATATAT TTGAGTTACT CTTAGGTATT TGCAAGCAAC TGATCTTTCT TTATCCCGT   2358
TTCTGGCTTA AACCTCATTA GAAATATATT ATAATGTCAC CTACTCTGTG GTTAAGACA  2418
TTCCCTTACA TTATAAGGTA TTTCACGTCG TATCAGGTCG AAAAAAATAA TGGTACGCTC  2478
TTTCTTATCA CAAATTTCTC TAACTTCTAG A                                2509
```

( 2 ) INFORMATION FOR SEQ ID NO:15:

( i ) SEQUENCE CHARACTERISTICS:
( A ) LENGTH: 359 amino acids
( B ) TYPE: amino acid
( D ) TOPOLOGY: linear ( i i ) MOLECULE TYPE: protein ( x i ) SEQUENCE DESCRIPTION: SEQ ID NO:15:

```
Met Ala Ala Ile Thr Leu Leu Gly Leu Leu Leu Val Ala Ser Ser Ile
 1               5                  10                  15

Asp Ile Ala Gly Ala Gln Ser Ile Gly Val Cys Tyr Gly Met Leu Gly
             20                  25                  30

Asn Asn Leu Pro Asn His Trp Glu Val Ile Gln Leu Tyr Lys Ser Arg
         35                  40                  45

Asn Ile Gly Arg Leu Arg Leu Tyr Asp Pro Asn His Gly Ala Leu Gln
     50                  55                  60

Ala Leu Lys Gly Ser Asn Ile Glu Val Met Leu Gly Leu Pro Asn Ser
 65                  70                  75                  80

Asp Val Lys His Ile Ala Ser Gly Met His Ala Arg Trp Trp Val
                 85                  90                  95

Gln Lys Asn Val Lys Asp Phe Trp Pro Asp Val Lys Ile Lys Tyr Ile
             100                 105                 110

Ala Val Gly Asn Glu Ile Ser Pro Val Thr Gly Thr Ser Tyr Leu Thr
         115                 120                 125

Ser Phe Leu Thr Pro Ala Met Val Asn Ile Tyr Lys Ala Ile Gly Glu
     130                 135                 140

Ala Gly Leu Gly Asn Asn Ile Lys Val Ser Thr Ser Val Asp Met Thr
145                 150                 155                 160

Leu Ile Gly Asn Ser Tyr Pro Pro Ser Gln Gly Ser Phe Arg Asn Asp
                 165                 170                 175

Ala Arg Trp Phe Val Asp Ala Ile Val Gly Phe Leu Arg Asp Thr Arg
             180                 185                 190
```

| | | | | | | | | | | | | | | |
|---|---|---|---|---|---|---|---|---|---|---|---|---|---|---|
| Ala | Pro | Leu 195 | Leu | Val | Asn | Ile | Tyr 200 | Pro | Tyr | Phe | Ser | Tyr 205 | Ser | Gly | Asn |
| Pro | Gly 210 | Gln | Ile | Ser | Leu | Pro 215 | Tyr | Ser | Leu | Phe | Thr 220 | Ala | Pro | Asn | Val |
| Val 225 | Val | Gln | Asp | Gly | Ser 230 | Arg | Gln | Tyr | Arg | Asn 235 | Leu | Phe | Asp | Ala | Met 240 |
| Leu | Asp | Ser | Val | Tyr 245 | Ala | Ala | Leu | Glu | Arg 250 | Ser | Gly | Gly | Ala | Ser 255 | Val |
| Gly | Ile | Val | Val 260 | Ser | Glu | Ser | Gly | Trp 265 | Pro | Ser | Ala | Gly | Ala 270 | Phe | Gly |
| Ala | Thr | Tyr 275 | Asp | Asn | Ala | Ala | Thr 280 | Tyr | Leu | Arg | Asn | Leu 285 | Ile | Gln | His |
| Ala | Lys 290 | Glu | Gly | Ser | Pro | Arg 295 | Lys | Pro | Gly | Pro | Ile 300 | Glu | Thr | Tyr | Ile |
| Phe 305 | Ala | Met | Phe | Asp | Glu 310 | Asn | Asn | Lys | Asn | Pro 315 | Glu | Leu | Glu | Lys | His 320 |
| Phe | Gly | Leu | Phe | Ser 325 | Pro | Asn | Lys | Gln | Pro 330 | Lys | Tyr | Asn | Ile | Asn 335 | Phe |
| Gly | Val | Ser | Gly 340 | Gly | Val | Trp | Asp | Ser 345 | Ser | Val | Glu | Thr | Asn 350 | Ala | Thr |
| Ala | Ser | Leu 355 | Val | Ser | Glu | Met | | | | | | | | | |

( 2 ) INFORMATION FOR SEQ ID NO:16:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO:16:

GGAATTCTGG TACCTCCCGG GAGGATCCAT CTAGAGCTCG AGTAAGCTTC 50

( 2 ) INFORMATION FOR SEQ ID NO:17:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO:17:

GGAATTCTGG TACCTCCCGG GAGGATCCAT CTAGAGCTCG AGTAAGCTTC 50